United States Patent [19]
Wilk

[11] Patent Number: 5,441,507
[45] Date of Patent: Aug. 15, 1995

[54] LAPAROSCOPIC OR ENDOSCOPIC ANASTOMOSIS TECHNIQUE AND ASSOCIATED INSTRUMENTS

[76] Inventor: Peter J. Wilk, 185 West End Ave., New York, N.Y. 10023

[21] Appl. No.: 212,104

[22] Filed: Apr. 11, 1994

Related U.S. Application Data

[60] Division of Ser. No. 981,251, Nov. 25, 1992, Pat. No. 5,330,486, which is a continuation-in-part of Ser. No. 921,510, Jul. 29, 1992, Pat. No. 5,258,008.

[51] Int. Cl.$^6$ ............................................. A61B 17/04
[52] U.S. Cl. ................................... 606/139; 128/898
[58] Field of Search ................... 606/139, 144–148, 606/151, 153, 219; 128/898; 227/179–181

[56] References Cited

U.S. PATENT DOCUMENTS

| | | | |
|---|---|---|---|
| 4,473,077 | 9/1984 | Noiles | 227/179 |
| 4,477,007 | 10/1984 | Foslien | 227/19 |
| 4,485,817 | 12/1984 | Swiggett | 227/179 |
| 4,488,523 | 12/1984 | Shichman | 227/179 |
| 5,042,707 | 8/1991 | Taheri | 227/179 |
| 5,197,649 | 3/1993 | Bessler et al. | 227/179 |
| 5,205,459 | 4/1993 | Brinkerhoff et al. | 227/179 |
| 5,261,920 | 11/1993 | Main et al. | 606/153 |
| 5,309,927 | 5/1994 | Welch | 128/898 |
| 5,314,435 | 5/1994 | Green et al. | 606/153 |
| 5,314,436 | 5/1994 | Wilk | 606/153 |
| 5,346,501 | 9/1994 | Regula et al. | 606/151 |

*Primary Examiner*—Gary Jackson
*Attorney, Agent, or Firm*—R. Neil Sudol; Henry D. Coleman

[57] ABSTRACT

A laparoscopic surgical technique for performing an anastomosis comprises the steps of disposing a laparoscopic trocar sleeve in a patient's abdominal wall, inserting a distal end of a laparoscopic instrument into an abdominal cavity of the patient through the trocar sleeve, and manipulating the instrument from outside the patient to loop a purse-string-type suture through a free end of a first severed intestinal segment of the patient. In other steps of the laparoscopic surgical technique, a flexible anastomosis-forming device is inserted through the patient's rectum so that an end cap at a distal end of the anastomosis device protrudes from a free end of a second severed intestinal segment of the patient. The anastomosis-forming device is shifted further through the patient's rectum so that the end cap is inserted into the first severed intestinal segment through the free end thereof. During the shifting of the end cap, the first severed intestinal segment is held with a laparoscopic tool from outside the patient to facilitate insertion of the end cap into the first severed intestinal segment. Upon insertion of the end cap into the first severed intestinal segment, the purse-string-type suture is drawn via a laparoscopic member to close the free end of the first severed intestinal segment about the end cap. The anastomosis-forming device is operated from outside the patient to connect the intestinal segments to one another in an anastomosis.

9 Claims, 10 Drawing Sheets

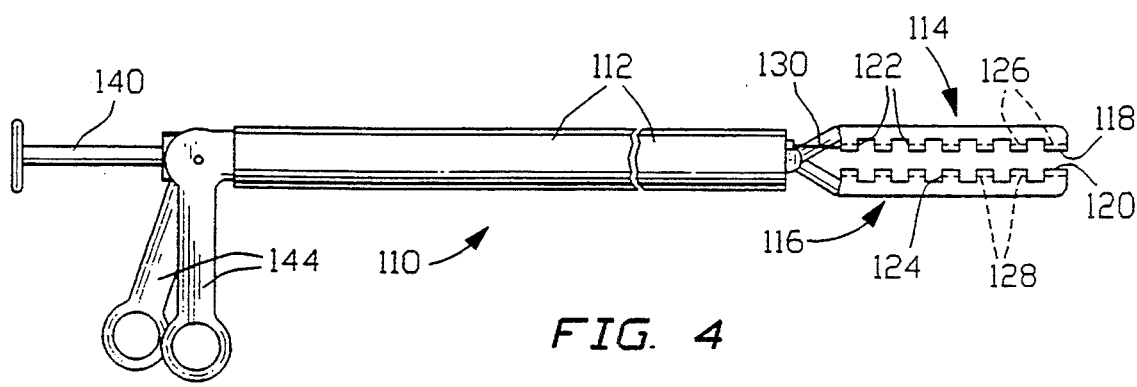
FIG. 4
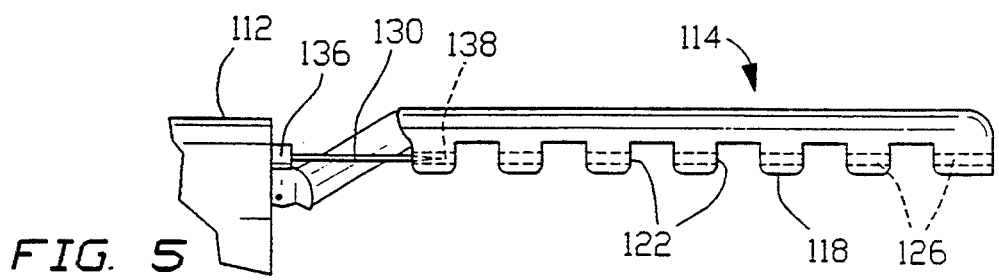
FIG. 5
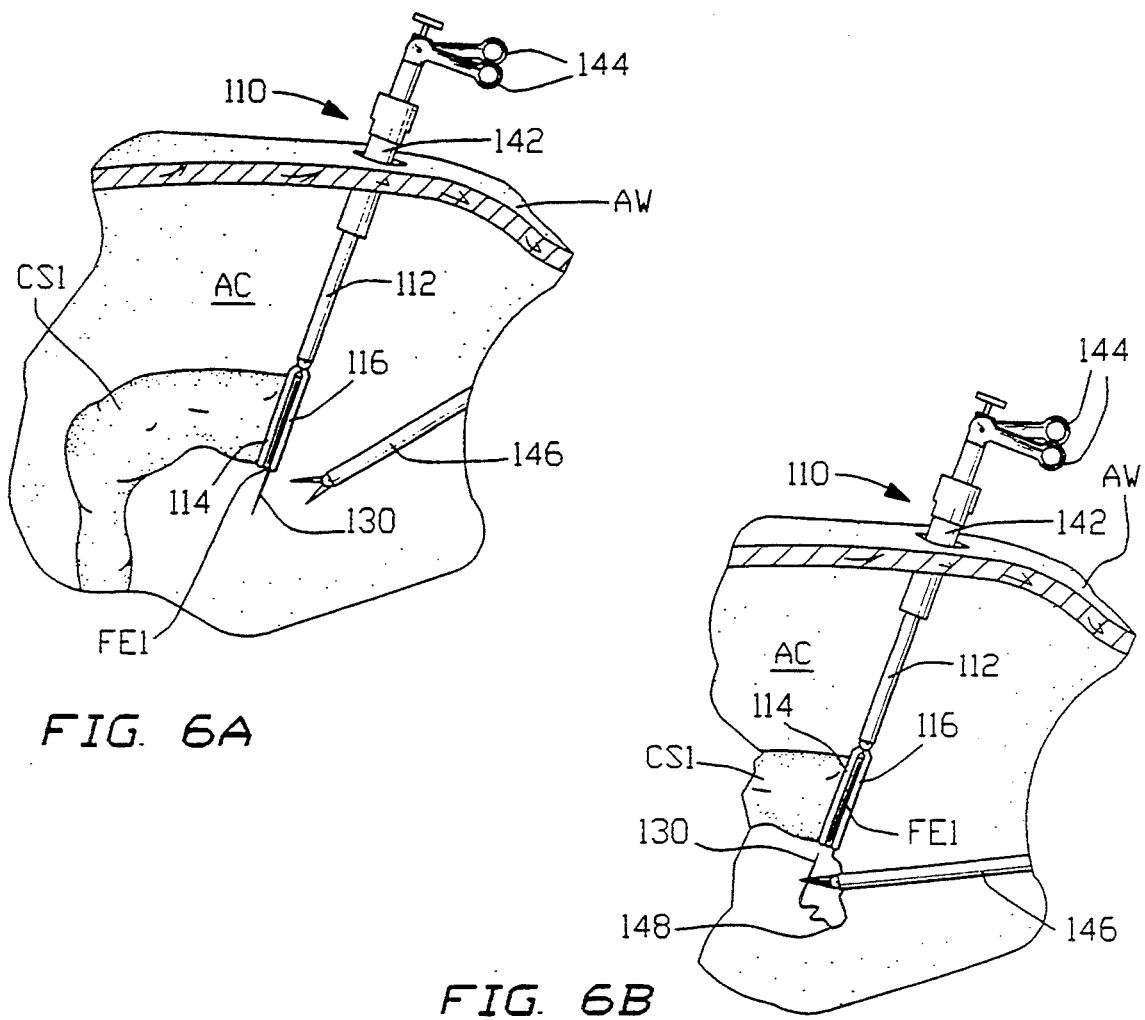
FIG. 6A
FIG. 6B

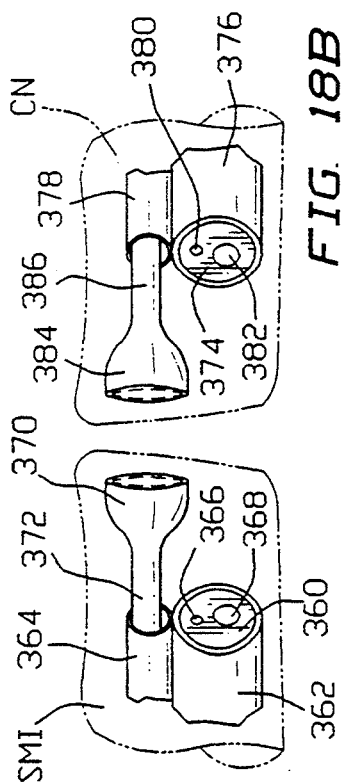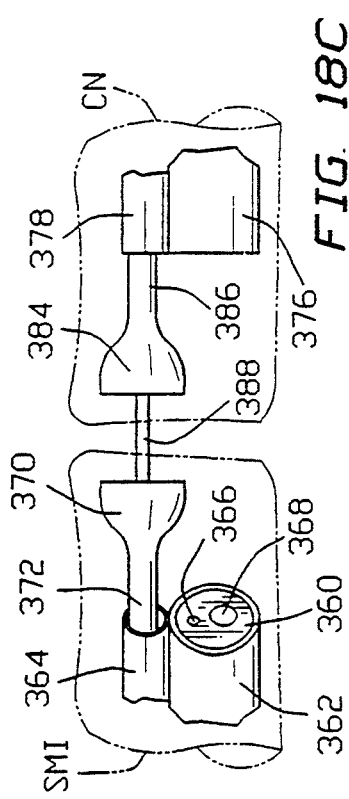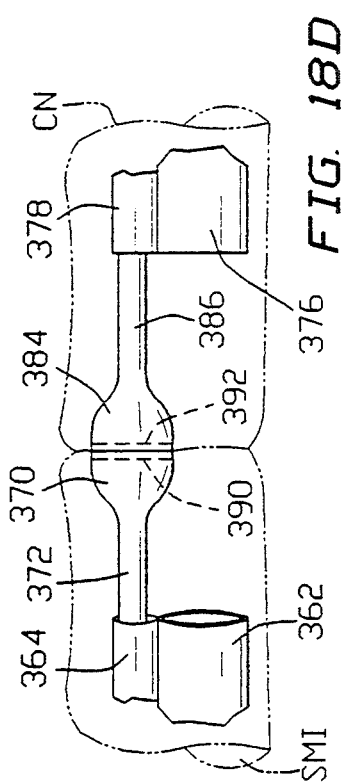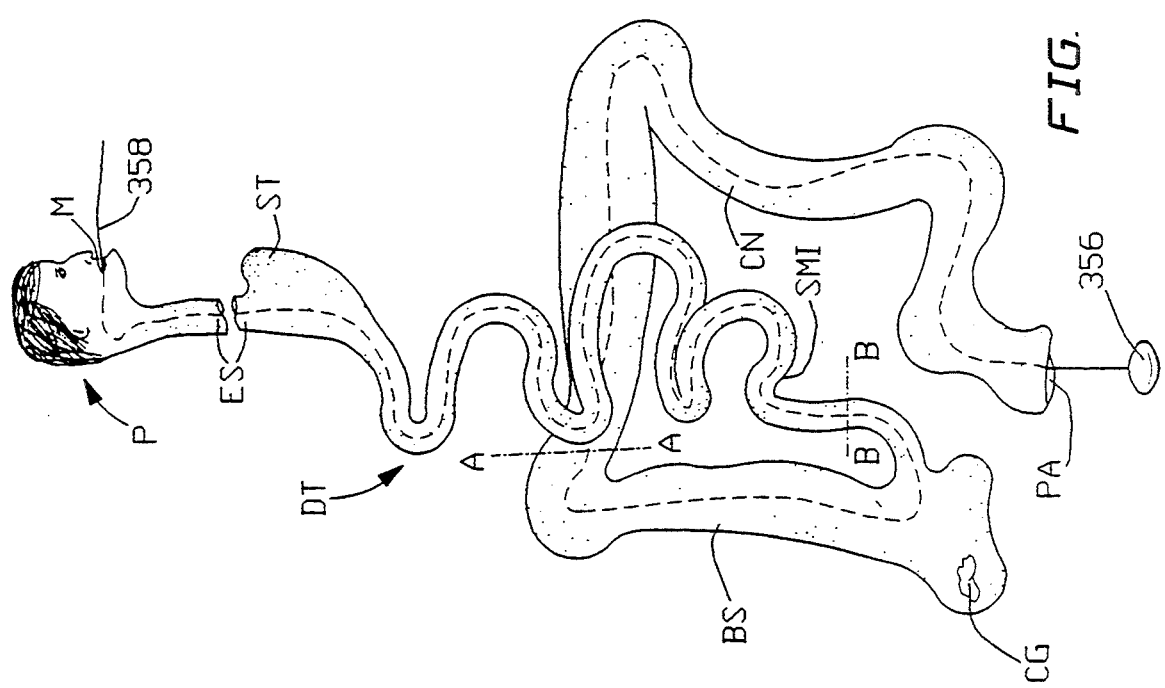

LAPAROSCOPIC OR ENDOSCOPIC ANASTOMOSIS TECHNIQUE AND ASSOCIATED INSTRUMENTS

CROSS REFERENCE TO A RELATED APPLICATION

This is a division of application Ser. No. 07/981,251 filed Nov. 25, 1992, now U.S. Pat. No. 5,830,486, which is a continuation-in-part of application Ser. No. 921,510 filed Jul. 29, 1992 now U.S. Pat. No. 5,258,008.

FIELD OF THE INVENTION

This invention relates to an anastomosis technique. More particularly, this invention relates to a laparoscopic or endoscopic anastomosis method and instrument assemblies for use in performing the method.

BACKGROUND OF THE INVENTION

Anastomosis staplers generally include multiple rows of staples, with a cutting blade disposed between adjacent rows. The blade is actuated subsequently to the firing of the staples.

There are at least two kinds of anastomosis operations. Linear gastro-intestinal anastomoses involve the use of linear multiple-fire surgical staplers which can sever, for example, an intestine while applying rows of staples to the severed organ on opposite sides of the cut. End-to-end or intra-luminal anastomoses involve the insertion into a tubular organ (e.g., an intestine) of staplers with circular arrays of staples fired in an axial direction.

Linear anastomoses staplers have multiple staples in linear arrays. The staples are fired between jaws which are maintained in a closed configuration during the firing of the staples. The staples are fired sequentially by an ejector rod with a camming surface at a distal end. As the rod is pushed in the distal direction, the staples are pushed in sequence from one jaw against the other jaw, which serves to close the staples in a conventional process.

During an end-to-end or intra-luminal anastomosis operation for connecting ressected bowel sections, a stapling member at the distal end of a rigid metal tube is inserted through a patient's rectum so that the stapling member is flush against a closed free end of an intestinal segment. Through an open-abdomen incision, an anvil member is inserted into another intestinal segment which is then closed at the free end, e.g., by a purse string suture which has been sewn around the mouth of the organ. The anvil member is then connected to the stapling member through the closed ends of the intestinal segments. The anvil member and the stapling member are brought close to one another via a screw mechanism in the metal tube, thereby clamping the closed ends of the intestinal segments to one another between the anvil and the stapling member. Subsequently, staples are ejected from the stapling member in a circular array, while the closed ends of the intestinal segments are cut along the array of staples, thereby forming an internal opening between the connected segments of intestine.

The above-described operation is open abdominal surgery and involves all of the procedures and safeguards necessary for such surgery. For example, because of extensive blood loss, the patient may have have to be provided with a transfusion.

OBJECTS OF THE INVENTION

An object of the present invention is to provide an anastomosis-forming procedure.

Another object of the present invention is to provide a laparoscopic or endoscopic surgical technique for forming an anastomosis.

A further object of the present invention is to provide an anastomosis stapling device particularly adapted for use in endoscopic or laparoscopic surgery.

Yet another object of the present invention is to provide a laparoscopic instrument assembly for use in forming a purse-string-type suture in an organ.

An additional, more particular, object of the present invention is to provide a flexible endoscopic stapling assembly for use in forming an anastomosis.

These and other objects of the present invention will be apparent from the drawings and detailed descriptions herein.

SUMMARY OF THE INVENTION

A surgical assembly comprises, in accordance with the present invention, a stapling device having a flexible shaft, an anvil portion and a stapling portion at a distal end of the shaft, and a first actuator, disposed in part at a proximal end of the shaft and operatively connected to the anvil portion and the stapling portion, for moving the anvil portion and the stapling portion towards one another to clamp at least one tubular organ segment in a stapling operation. The stapling device of the surgical assembly also has a second actuator, disposed in part at a proximal end of the shaft and operatively connected to the stapling portion, for ejecting a plurality of staples essentially simultaneously from the stapling portion towards the anvil portion upon a clamping of a tubular organ segment. The surgical assembly further comprises an illumination guide connected to the stapling device for guiding light from the proximal end to the distal end of the stapling device. An image guide is connected to the stapling device for transmitting an image from the distal end to the proximal end.

According to a specific embodiment of the present invention, each of the anvil portion and the stapling portion includes a plurality of segments movably secured to one another, whereby the anvil portion and the stapling portion can alternately assume different arcuate configurations, thereby enabling a flexing of the anvil portion and the stapling portion during an endoscopic insertion operation. In this embodiment of the invention, the surgical assembly may additionally comprise means for stiffening the anvil portion and the stapling portion prior to an operation of the second actuator. The means for stiffening serves to rigidify the anvil portion and the stapling portion in a predetermined configuration, e.g. a linear configuration. In accordance with a particular implementation of this embodiment of the invention, the segments are provided with mating projections and recesses, the projections being slidably inserted into corresponding recesses.

In another embodiment of the present invention, the stapling device is an anastomosis-forming device and the staples are arranged in an endless type configuration. In one implementation of this embodiment of the invention, the staples are oriented in a transverse direction relative to the shaft and are ejected from the stapling portion in the transverse direction. Preferably, the endless type configuration is substantially rectangular. In another implementation of this embodiment of the invention, the staples are oriented in an axial direction relative to the shaft and are ejected from the stapling portion in the axial direction.

According to another feature of the present invention, the surgical assembly further comprises a sheath member with an expandable biopsy-type channel, the stapling device being inserted into the channel, the illumination guide and the image guide being attached to the sheath.

Where the stapling device is an anastomosis-forming device, the staples are arranged in a substantially linear configuration.

A method for connecting two hollow organs so that the organs communicate with one another comprises, in accordance with the present invention, the steps of (a) inserting a flexible fiber optic endoscope assembly through an opening in a patient into a first hollow organ of the patient, (b) utilizing light-transmitting componentry of the endoscope assembly to visually inspect the first hollow organ internally during the step of inserting, and (c) ejecting from a distal end of the endoscope assembly a stapling device with a flexible shaft and a first staple forming member at a distal end of the shaft upon insertion of the endoscope assembly to a desired surgical site inside the first hollow organ, as determined via the endoscopic visual inspection. Other steps in the surgical method include (d) moving the first staple forming member towards a cooperating second staple forming member disposed in a second hollow organ, thereby clamping walls of the first and the second hollow organ to one another between the staple forming members, and (e) firing a plurality of staples in an endless type configuration from one of the staple forming members through the walls of the organs towards the other staple forming member in essentially a single stapling operation. The staples are closed during the firing or ejection thereof, thereby stapling the hollow organs to one another at the surgical site. In an area enclosed by the fired staples, substantially aligned apertures are cut in the hollow organs. Subsequently, the staple forming members are removed from the connected hollow organs.

In accordance with another feature of the present invention, the surgical method further comprises the steps of inserting the second staple forming member into an abdominal cavity of the patient through a laparoscopic trocar sleeve disposed in an abdominal wall of the patient, cutting a perforation in a wall of the second hollow organ, and inserting the second staple forming member through the perforation into the second hollow organ. The perforation is closed at some point following insertion of the second staple forming-member into the second hollow organ. The perforation may be closed prior to the removal of the staple forming members from teh hollow organs, in which case the second staple forming member is removed with the first staple forming member through the opening in the patient.

Alternatively, the second staple forming member may be extracted through the perforation while the first staple forming member and the shaft are pulled through the opening in the patient. In this alternative, the perforation is closed and the second staple forming member is withdrawn through the trocar sleeve upon extraction of the second staple forming from teh second hollow organ.

It is to be noted that the first staple forming member and a distal end portion of the shaft attached thereto may be moved into the abdominal cavity of the patient through a respective trocar sleeve disposed in the abdominal wall of the patient. In this event, the opening in the patient is an incision formed in the skin surface of the patient.

Where the second hollow organ is an elongate tubular organ (e.g., an intestine) and the organ walls include a sidewall of the second hollow organ (e.g., in a side-to-side or side-to-end anastomosis), the surgical method further comprises the steps of severing a free end of the second hollow organ along a cut line, inserting a linear multiple-fire stapling device through a laparoscopic trocar sleeve into the patient's abdomen, and using the multiple-fire stapling device to staple the second hollow organ along the cut line upon insertion of the second staple forming member into the second hollow organ.

In a surgical method in accordance with the present invention, the staples may be fired in a transverse direction relative to the shaft of the stapling device.

Where the opening in the patient is the mouth (a natural opening), the first hollow organ is the duodenum, and the second hollow organ is the common bile duct, the endoscope assembly is inserted through the mouth, the esophagus, and the stomach so that the stapling device is ejected into a part of the duodenum.

In accordance with another feature of the present invention, the staple forming memebrs are moved towards one another by exerting an attractive magnetic force between the staple forming members.

In accordance with a particular embodiment of the surgical method, the method further comprises the steps of inserting an additional endoscope assembly into the second hollow organ, and utilizing light-transmitting componentry of the additional endoscope assembly during the insertion of the additional endoscope assembly to visually inspect the second hollow organ internally. Upon insertion of the additional endoscope assembly to a desired surgical site inside the second hollow organ, as determined by the utilization of light-transmitting componentry of the additional endoscope assembly, the second staple forming member is ejected from a distal end of the additional endoscope assembly, the second staple forming member being connected to a flexible shaft. The additional endoscope assembly may comprise a flexible fiber optic endoscope assembly.

In accordance with this embodiment of the surgical method, the removal of the staple forming members includes the step of withdrawing the second staple forming member from the second hollow organ along a path of insertion of the additional endoscope assembly and the second staple forming member.

Where the second hollow organ is the small intestine, the surgical method may further comprise the steps of passing a string through the patient from the patient's mouth to the rectum and following the string with the additional endoscope assembly during the insertion of the additional endoscope assembly.

A method for forming an anastomosis comprises, in accordance with the present invention, the steps of (i) inserting into a first hollow organ part a stapling device including a stapling member with a plurality of staples in an endless type configuration, the stapling member being attached to a distal end of an elongate shaft, (ii) inserting into a second hollow organ part an anvil member, (iii) juxtaposing a first side wall of the first hollow organ part to a second side wall of the second hollow organ part, (iv) clamping the first side wall and the second side wall to one another between the stapling member and the anvil member, (v) firing, from the stapling member towards the anvil member in essentially a single stapling operation, the plurality of staples in a common direction transverse relative to the shaft at the distal end thereof, (vi) closing the staples during the step of firing, thereby stapling the first hollow organ part to the second hollow organ part, in an area enclosed by the fired staples, (vii) cutting substantially aligned apertures in the first hollow organ part and the second hollow organ part, and (viii) removing the stapling member and the anvil member from the first and the second hollow organ part.

According to another feature of the present invention, the anastomosis method further comprises the steps of inserting at least one of the anvil member and the stapling member into an abdominal cavity of the patient through a laparoscopic trocar sleeve disposed in an abdominal wall of the patient, and cutting a perforation in a wall of one of the hollow organ parts, the selected one of the anvil member and the stapling member being inserted through the perforation.

According to an additional feature of the present invention, the anastomosis method further comprises the step of closing the perforation upon insertion of the anvil member or the stapling member into the respective organ part.

Where the the anvil member is inserted through the perforation and the perforation is closed prior to the removal of the anvil member and the stapling member from the organ parts, the anvil member is removed with the stapling member through the first hollow organ part.

According to another feature of the present invention, the step of clamping the organs includes the step of exerting an attractive magnetic force between the anvil member and the stapling member.

Where the anvil member is isnerted through the perforation and the anvil member is subsequently extracted through the perforation while the stapling member and the shaft are pulled through the opening in the patient, the anastomosis method further comprises the steps of closing the perforation and withdrawing the anvil member through the trocar sleeve upon extraction fo the anvil member out through the perforation.

A method for performing a choledocoduodenostomy comprises, in accordance with the present invention, the steps of (1) inserting a flexible fiber optic endoscope assembly through a patient's mouth, the esophagus, and the stomach, (2) utilizing light-transmitting componentry of the endoscope assembly during the step of inserting to visually inspect tissues along an insertion path, (3) upon insertion of the endoscope assembly to a desired surgical site inside the duodenum of the patient, as determined by utilizing the light-transmitting componentry of the endoscope assembly, ejecting from a distal end of the endoscope assembly a stapling device having a flexible shaft and a first staple forming member at a distal end of the shaft, (4) inserting a second staple forming member through an abdominal wall and the liver of the patient and into the common bile duct, (5) clamping walls of the common bile duct and the duodenum to one another between the staple forming members, (6) in essentially a single stapling operation, firing a plurality of staples in an endless type configuration from one of the staple forming members through the walls towards the other of the staple forming members, (7) closing the staples during the step of firing, thereby stapling the duodenum to the common bile duct, (8) cutting substantially aligned apertures in the walls of the duodenum and the common bile duct, and (9) removing the staple forming members from the duodenum and the common bile duct.

Pursuant to another feature of the present invention, the first staple forming member is a stapling member and the second staple forming member is an anvil member.

A method for forming an anastomosis comprises, in accordance with the present invention, the steps of (a) inserting into a first hollow organ part a magnetic element having an annular form, (b) inserting, into a second hollow organ part, elements for cooperating with the magnetic element to form an annular magnetic clamp, (c) magnetically clamping walls of the first and the second hollow organ part between the magnetic element and the cooperating elements, (d) inserting a fiber optic guide into one of the first and the second hollow organ part, (e) emitting a laser beam from a distal end of the fiber optic guide, and (f) using the laser beam to cut aligned apertures in the clamped walls the first and the second hollow organ part.

Pursuant to another feature of the present invention, the magnetic anastomosis method further comprises the steps of (g) inserting either the magnetic element or the cooperating element(s) into an abdominal cavity of the patient through a laparoscopic trocar sleeve disposed in an abdominal wall of the patient, and (h) forming a perforation in a wall of one of the hollow organ parts, the inserted one of the magnetic element and the cooperating elements being inserted through the perforation.

Pursuant to a further feature of the present invention, the cooperating elements may include a multiplicity of magnetizable elements such as metal filings or small metal rods.

Pursuant to yet another feature of the present invention, the magnetizable elements are injected via a needle into the respective hollow organ part.

A surgical method for performing an anastomosis comprises, in accordance with the present invention, the steps of (i) disposing a laparoscopic trocar sleeve in a patient's abdominal wall, (ii) inserting a distal end of a laparoscopic instrument into an abdominal cavity of the patient through the trocar sleeve, (iii) manipulating the instrument from outside the patient to loop a purse-string-type suture through a free end of a first severed intestinal segment of the patient, (iv) moving a flexible anastomosis-forming device through the patient's rectum so that an end cap at a distal end of the anastomosis device protrudes from a free end of a second severed intestinal segment of the patient, (v) shifting the anastomosis-forming device further through the patient's rectum so that the end cap is inserted into the first severed intestinal segment through the free end thereof, (vi) during the step of shifting, holding the first severed intestinal segment with a laparoscopic tool from outside the patient to facilitate insertion of the end cap into the first severed intestinal segment, (vii) upon insertion of the end cap into the first severed intestinal segment, drawing the purse-string-type suture via a laparoscopic member to close the free end of the first severed intestinal segment about the end cap, and (viii) operating the anastomosis-forming device from outside the patient to connect the first and the second severed intestinal segment to one another in an anastomosis.

According to another feature of the present invention, the method further comprises the step of using an endoscopic visual system to visually inspect the second severed intestinal segment internally prior to the step of shifting. The visual inspection is useful to enabling a proper winding of the anastomosis-forming device through the intestine. In a specific embodiment of the invention, the visualization is performed during the moving of the anastomosis-forming device through the second intestinal segment. In that case, the endoscopic visual system is entrained to the anastomosis-forming device. In an alternative specific embodiment of the invention, the visualization is effectuated prior to the movement of the anastomosis-forming device through the second intestinal segment. In the latter case, the endoscopic visual system may be attached to a sheath member with an expandable biopsy-type channel, the anastomosis-forming device being pushed through the channel subsequently to the insertion of the endoscope.

According to another feature of the present invention, the laparoscopic instrument comprises a laparoscopic grasping forceps. Then, the manipulation of the laparoscopic instrument includes the steps of grasping or holding a needle inside the patient's abdominal cavity and maneuvering the needle with the forceps.

According to a further feature of the present invention, the method further comprises the steps of inserting a laparoscopic clamp into the patient's abdominal cavity and clamping the first severed intestinal segment with the clamp. In that event, the maneuvering of the needle including the step of threading the needle through passages in the clamp.

According to an additional feature of the present invention where the end cap comprises an anvil member of the anastomosis-forming device, the step of operating the anastomosis-forming device includes the step of ejecting staples from a stapling portion of the anastomosis-forming device towards the anvil member upon a shifting of the intestinal segments towards one another to clamp the segments to one another.

According to yet another feature of the present invention, the method also comprises the step, performed prior to the shifting of the end cap into the first intestinal segment from the second end segment, of manipulating the laparoscopic instrument from outside the patient to loop an additional purse-string-type suture through a free end of the second severed intestinal segment. The method also comprises the step of drawing the additional purse-string-type suture via a laparoscopic member to close the free end of the second severed intestinal segment about the stapling member, upon an ejection of the end cap from the second severed intestinal segment.

A laparoscopic instrument assembly comprises, in accordance with the present invention, an elongate shaft, and an elongate suturing guide member attached to the shaft at a distal end thereof. The guide member is provided with a plurality of spaced recesses for receiving organic tissues of a patient upon engagement of the guide member and the tissues. The guide member is further provided with passages for enabling the threading of a needle and suture through tissues received in the recesses.

Pursuant to another feature of the present invention, the passages in the suturing guide member are aligned with one another, each of the passages communicating at opposite ends with two of the recesses.

Pursuant to a further feature of the present invention, the guide member is one of a pair of clamping jaws movably secured to the shaft at the distal end thereof. Each of the jaws is provided with a plurality of spaced recesses for receiving organic tissues of the patient upon engagement of the respective jaw and such organic tissues. Each of the jaws is also provided with passages for enabling the threading of a needle and suture through tissues received in the recesses of the respective one of the jaws.

Pursuant to yet another feature of the present invention, the assembly further comprises means coupled to the shaft for ejecting a needle through the passages upon an engagement of the tissues by the guide member.

A surgical assembly comprises, in accordance with the present invention, an anastomosis-forming device, an illumination guide connected to the anastomosis-forming device for guiding light from the proximal end of the anastomosis-forming device to the distal end thereof, and an image guide connected to the anastomosis-forming device for transmitting an image from the proximal end to the distal end. The anastomosis-forming device has a flexible shaft, an anvil portion and a stapling portion at a distal end of the shaft, a first actuator at a proximal end of the shaft for moving the anvil portion and the stapling portion towards one another to clamp two tubular organ segments to one another in an anastomosis operation, and a second actuator at a proximal end of the shaft for ejecting staples from the stapling portion towards the anvil portion.

Pursuant to another feature of the present invention, this surgical assembly further comprises a sheath member with an expandable biopsy-type channel. The anastomosis-forming device is inserted into the channel, while the illumination guide and the image guide are attached to the sheath.

The instrument assemblies and method in accordance with the present invention enable the performance of intestinal anasotomoses with less trauma to the patient than in conventional incision-based surgery. Laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

BRIEF DESCRIPTION OF THE DRAWING

FIG. 4 is a schematic side elevational view of a laparoscopic instrument in accordance with the present invention, for forming a purse-string-type suture in a method in accordance with the present invention.

FIG. 5 is a side elevational view showing a detail of FIG. 4 on an enlarged scale.

FIGS. 6A through 6C are each a schematic cross-sectional view, showing a patient's abdomen during a laparoscopic procedure. FIGS. 6A–6C illustrate successive steps in the use of the instrument of FIGS. 4 and 5.

FIG. 18A is a schematic diagram of a person's digestive tract, showing an initial step in a ressection and anastomosis operation in accordance with the present invention.

FIGS. 18B-18D are schematic-side elevational views showing successive steps in the ressection and anastomosis operation partially illustrated in FIG. 18A.

DETAILED DESCRIPTION

Figure 1:
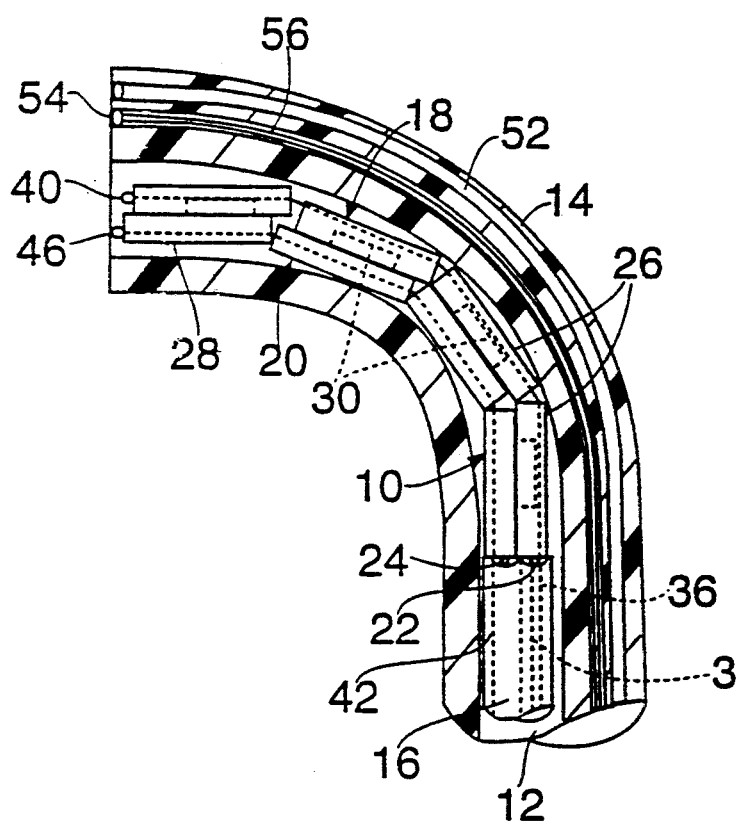
FIG. 1 is a partial schematic longitudinal cross-sectional view, on an enlarged scale, through a distal end of an endoscope insertion member, showing an endoscopic multiple fire stapling device.

FIG. 1 illustrates a multiple fire surgical stapler 10 inserted in a biopsy channel 12 of a flexible endoscope insertion member 14. Stapler 10 comprises an elongate flexible frame or shaft 16 and a stapling jaw 18 and an anvil jaw 20 movably secured to one another and to shaft 16 at one or more pivot pins 22 and 24. Each jaw 18 and 20 includes a plurality of segments 26 and 28 movably secured to one another, whereby jaws 18 and 20 can alternately assume different configurations such as an arcuate configuration shown in FIG. 1.

Stapler 10 further comprises a plurality of staples 30 mounted to jaw 18 for ejection towards jaw 20 under the action of a firing mechanism including a flexible rod 32 operatively connected to and longitudinally traversing shaft 16. A distal end of rod 32 is provided with a camming surface 34 (FIG. 2) for engaging and ejecting staples 30 in a transverse direction upon a longitudinal motion of rod 32.

Surgical stapler 10 additionally includes a mechanically acting tensioning device or wire 36 extending through channels 38 in segments 26 and fastened at a distal end 40. Wire 36 serves to stiffen or rigidify jaw 18 in a linear configuration prior to an actuation of firing rod 32. Similarly, another tensioning device or wire 42 extending through channels (not illustrated) in segments 28 and fastened at a distal end 46 serves to rigidify jaw 20 in a linear configuration prior to a multiple fire stapling operation.

Figure 2:
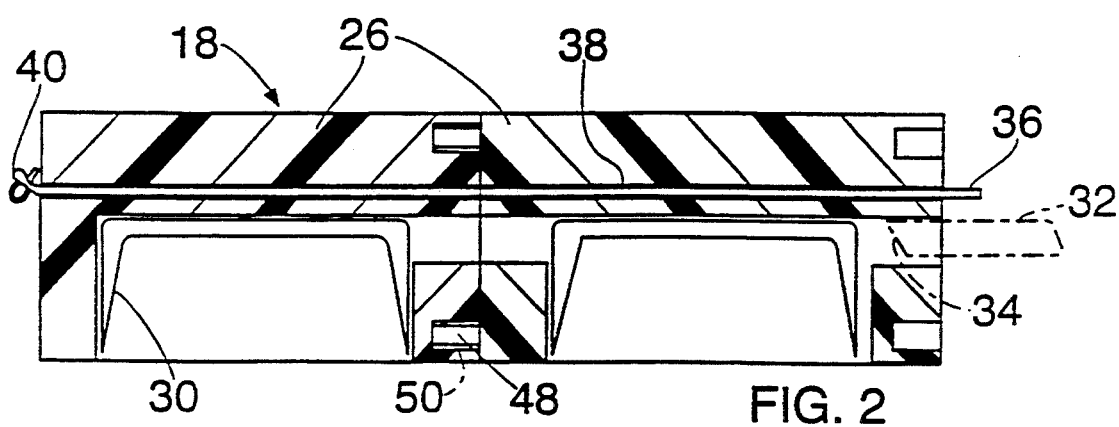
FIG. 2 is a partial schematic longitudinal cross-sectional view, on a larger scale, of a distal end portion of the endoscopic multiple fire stapling device of FIG. 1.

As illustrated in FIG. 2, jaw segments 26 are provided with mating projections 48 and recesses 50, projections 48 being slidably inserted into corresponding recesses 50.

Shaft 16 is flexible and has a diameter smaller than biopsy channel 12. Upon an insertion of endoscope insertion member 14 with stapler 10 into a patient's colon, for example, illuminating radiation is conducted into the patient via an illumination light guide 52. Light reflected from internal organic structures of the patient is then focused by a lens 54 onto a distal end of a fiber optic image guide 56. In response to images transmitted to an eyepiece (not shown) or monitor (not shown) via image guide 56, a surgeon or endoscopist pushes tubular shaft 16 to eject jaws 18 and 20 from the distal end of insertion member 14. Either prior to or after the ejection, wires 36 and 42 are pulled in the proximal direction to straighten and rigidify jaws 18 and 20.

Upon ejection of jaws 18 and 20 and the stiffening thereof via wires 36 and 42, the jaws are opened, for example, by continued tension on wires 36 and 42. Alternatively, additional tension elements or biasing springs (not illustrated) may be provided for opening jaws 18 and 20. Jaws 18 and 20 are then disposed about tissues to be stapled. Closure may be effectuated by pushing an auxiliary tubular member (not shown) about the jaws. Alternatively, the jaws may be operated as conventional endoscopic forceps.

Upon the closure of jaws 18 and 20 about the target tissues, rod 32 is shifted in the distal direction through to eject staples 30 from jaw 18. Staples 30 are closed by being forced against camming anvils (not illustrated) in jaw 20. Such camming anvils take a well known conventional form.

It is to be noted that the segments 26 (28) of jaw 18 (20) are articulated to one another. Accordingly, jaws 18 and 20 are bent during insertion into a patient by pivoting segments 26 and 28 relative to each other, whereby each of the jaws assumes different configurations at successive times.

Figure 3:
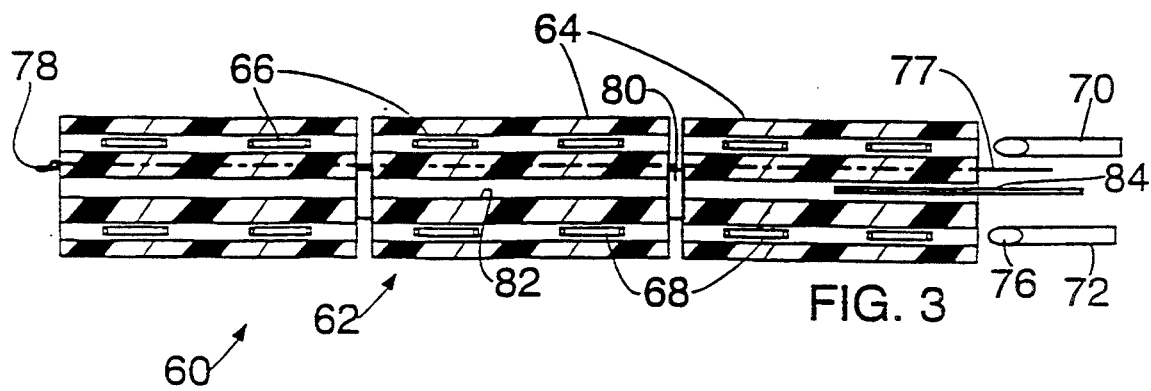
FIG. 3 is a partial schematic longitudinal cross-sectional view, on an enlarged scale, of a distal end portion of another multiple fire stapling device.

As illustrated in FIG. 3, another multiple fire surgical stapler 60 comprises a jaw 62 including a plurality of articulated or pivoted segments 64 for enabling jaw 62 to alternately assume a straight and different arcuate configurations.

Stapler 60 further comprises a first plurality of staples 66 arranged in a first row and a second plurality of staples 68 disposed in a second row parallel to staples 66. Staples 66 and 68 are ejectable towards an anvil carrying jaw (not shown) under the action of a pair of firing rods 70 and 72 each including a camming surface 74 and 76 at a distal end. Rods 70 and 72 are operatively connected to and longitudinally traversing a shaft (not shown) to which jaw 62 is pivotably connected.

Surgical stapler 60 additionally includes a mechanically acting tensioning device or wire 77 extending through segments 64 and fastened at a distal end 78. Wire 76 serves to stiffen or rigidify jaw 62 in a linear configuration prior to an actuation of firing rods 70 and 72 in a multiple firing operation.

As illustrated in FIG. 3, jaw segments 64 are provided with projections 80 slidably extending into corresponding recesses (not shown). Segments 64 are provided with longitudinally extending and alignable slots 82 for receiving a cutting blade 84 upon a common ejection stroke of rods 70 and 72.

In the event that stapler 60 is an endoscopic device, blade 84 is sufficiently flexible to allow for bending during an endoscopic insertion procedure.

As illustrated in FIGS. 4 and 5, a laparoscopic instrument assembly 110 comprises an elongate shaft 112, and a pair of elongate suturing guide members 114 and 116 pivotally attached as jaws to shaft 112 at a distal end thereof. Each suturing guide member or jaw 114 and 116 is provided along a respective inner face 118 and 120 with a plurality of spaced recesses 122 and 124 for receiving organic tissues of a patient upon engagement of the respective jaw and the organic tissues during a closure of the jaws and a concomitant clamping the tissues. Jaws 114 and 116 are further provided with respective longitudinally extending passages 126 and 128 for enabling the threading of a flexible needle 130 and suture 132 (FIG. 6B) through tissues received in recesses 122 and 124.

Passages 126 in jaw 114 are aligned with one another. Each passage 126 communicates at opposite ends with two recesses 122. Similarly, passages 128 in jaw 116 are aligned with one another and communicate at opposite ends with respective pairs of recesses 124.

As further illustrated in FIGS. 4 and 5, a distal end of needle 130 projects from a tube 136 extending along shaft 112. The tip of needle 130 is inserted into a most proximal passage 138 of passages 126 in jaw 114. Upon an opening of jaws 114 and 116 prior to a clamping operation, needle 130 flexes with jaw 114 so that the distal tip of the needle remains inserted into passage 138. A plunger or ejector rod 140 is slidably inserted into tube 136 to eject needle 130 through passages 126 and organic tissues in recesses 122 upon a closure of jaws 114 and 116 about a tubular organ.

Figure 6C:
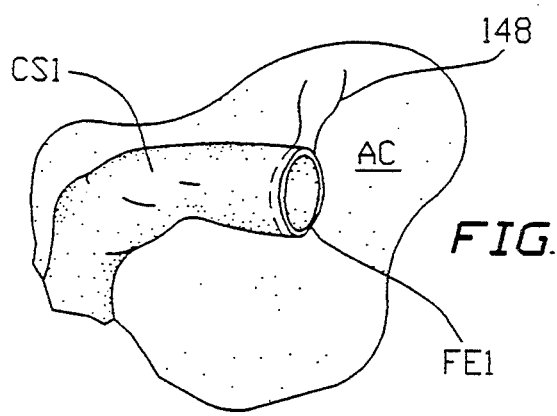

As depicted in FIG. 6A, a laparoscopic trocar sleeve 142 is disposed in a patient's abdominal wall AW and a distal end of instrument assembly 110 is inserted into an abdominal cavity AC of the patient through the trocar sleeve. Actuator handles 144 at the proximal end of shaft 112 are used to open jaws 114 and 116, whereupon instrument assembly 110 is manipulated from outside the patient to close jaws 114 and 116 about a ressected or severed colon segment CS1. Upon a clamping of colon or intestinal segment CS1 by jaws 114 and 116 so that portions of the colon tissues are pressed into recess 122 and 124, plunger rod 140 is pushed in a distal direction to eject needle 130 from tube 136 and through passages 126 in jaw 114 until at least a distal end portion of the needle emerges from jaw 114, as illustrated in FIG. 6A. A grasping forceps 146 inserted through another trocar sleeve (not shown) is then used to pull needle 130 and a suture 148 attached thereto from jaw 114. Forceps 146 is manipulated from outside the patient to insert needle 130 through passages 128 in jaw 116 and through colon tissues disposed in recesses 124. Instrument assembly 110 is thus used to loop a purse-string-type suture through a free end FE1 of colon segment CS1, as shown in FIG. 6C.

It is to be noted that jaws 114 and 116 may be provided at distal ends with hooks or flanges (not shown) and a latch (not shown) for facilitating a clamping of recalcitrant tissues. A first laparoscopic grasping forceps is used to grasp the hooks to draw the jaws 114 and 116 closer together, while a second laparoscopic grasping forceps is used to lock the latch. In that way, the entry of organic tissues into recesses 122 and 124 is ensured prior to the threading of needle 130 through passages 126 and 128.

Figure 7:
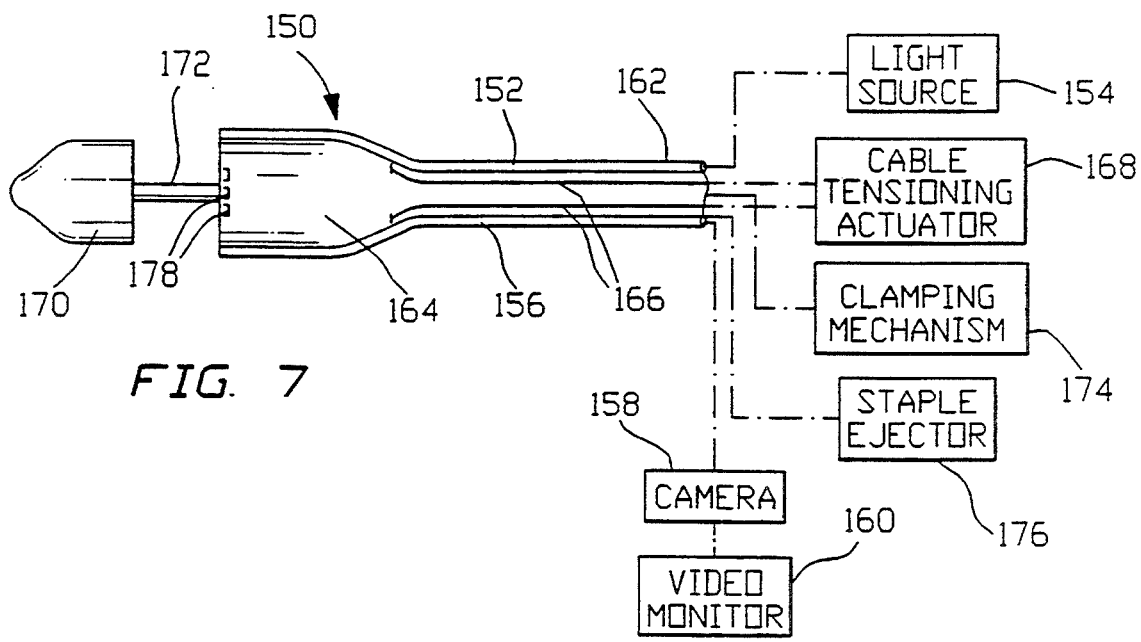
FIG. 7 is partially a schematic side elevational view and partially a block diagram of another laparoscopic instrument in accordance with the present invention, for use in forming an anastomosis in a method in accordance with the present invention.

As illustrated in FIG. 7, an endoscopic surgical assembly for use during a laparoscopic anastomosis procedure comprises an anastomosis-forming device 150, an illumination guide 152 connected to the anastomosis-forming device for guiding light from a light source 154 at a proximal end to the distal end of device 150. An image guide 156 is connected to anastomosis-forming device 150 for transmitting an image from the distal end of the device 150 to a camera 158 and a video monitor 160 at the proximal end. Anastomosis-forming device has a flexible shaft 162 which is oriented at the distal end, in the region of a stapling head 164 by cables 166 whose tension is controlled by an actuator 168. Stapling head 164 is connected to an anvil in the form of an end cap 170 via a rod 172 which moves longitudinally in response to a clamping actuator mechanism 174 to bring anvil 170 and the stapling head 164 towards one another to clamp two tubular organ segments SC1 and SC2 (see FIG. 9) to one another in an anastomosis operation. A staple ejector actuator 176 is provided in part at a proximal end of shaft 162 for ejecting staples 178 from stapling head 164 towards anvil 170.

Figure 8:
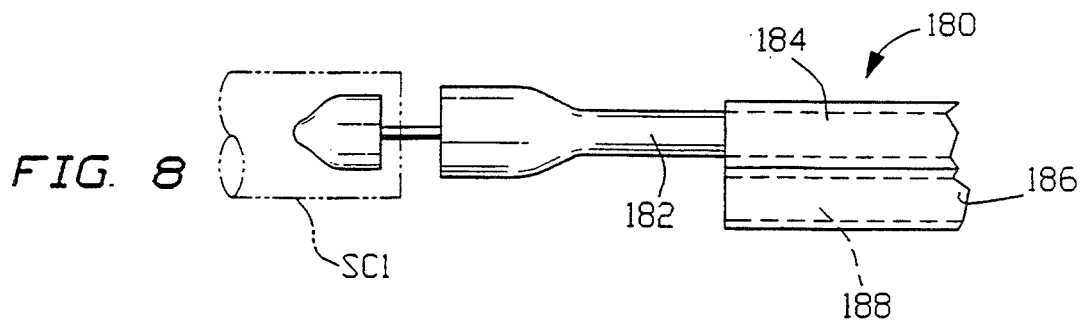
FIG. 8 is a partial schematic side elevational view of another laparoscopic instrument in accordance with the present invention, for use in forming an anastomosis in a method in accordance with the present invention.

As illustrated in FIG. 8, another endoscopic surgical assembly 180 comprises a flexible anastomosis-forming device 182 inserted through an expandable biopsy-type channel 184 of a sheath 186 which also encloses an endoscope 188.

Figure 9:
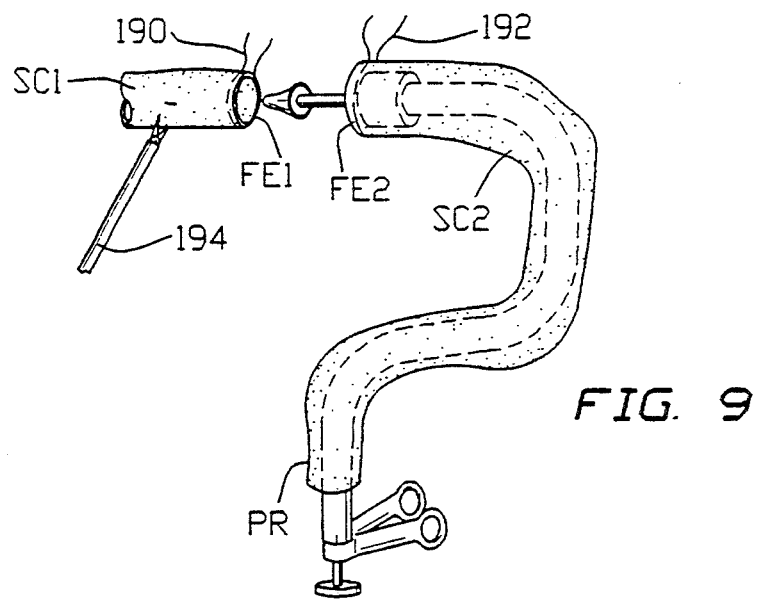
FIG. 9 is a schematic side elevational view of a ressected bowel section, showing a step in the performance of an anastomosis in accordance with the present invention.

During a laparoscopic anastomosis operation, the procedure of FIGS. 6A through 6C is used to apply purse-string type sutures to free ends FE1 and FE2 of both colon segment CS1 and intestinal segment SC2 (see FIG. 9). Upon the disposition of purse-string type sutures 190 and 192 about free ends FE1 and FE2, flexible anastomosis-forming device 150 is inserted through the patient's rectum PR so that anvil 170 protrudes from free end FE2 of colon segment SC2, as illustrated in FIG. 9. Suture 192 is then drawn closed about rod 172. Anastomosis-forming device 150 is then shifted further through rectum PR so that anvil 170 is inserted into colon segment SC1 through the free end thereof. During this operation, colon segment SC1 may be held or maneuvered by a laparoscopic grasping tool 194 to faciliate the insertion of anvil 170.

Upon an insertion of anvil 170 into intestinal segment SC1, purse-string-type suture 190 is drawn closed via a laparoscopic grasping member (e.g., tool 194 or another grasping forceps) to close free end FE1 of segment SC1 about anvil 170. Anastomosis-forming device 150 may then be operated from outside the patient to connect segments SC1 and SC2 to one another in an anastomosis.

It is to be noted that in the event that the instrument assembly of FIG. 8 is used to perform a laparoscopic anastomosis operation, endoscope 188 is first inserted into the patient with biopsy channel 184 of sheath 186 in a collapsed configuration. Upon the arrival of the distal end of the endoscope at the free end FE2 of the rectal colon segment SC2, anastomosis-forming device 182 is then inserted through the biopsy channel 184.

Figure 10:
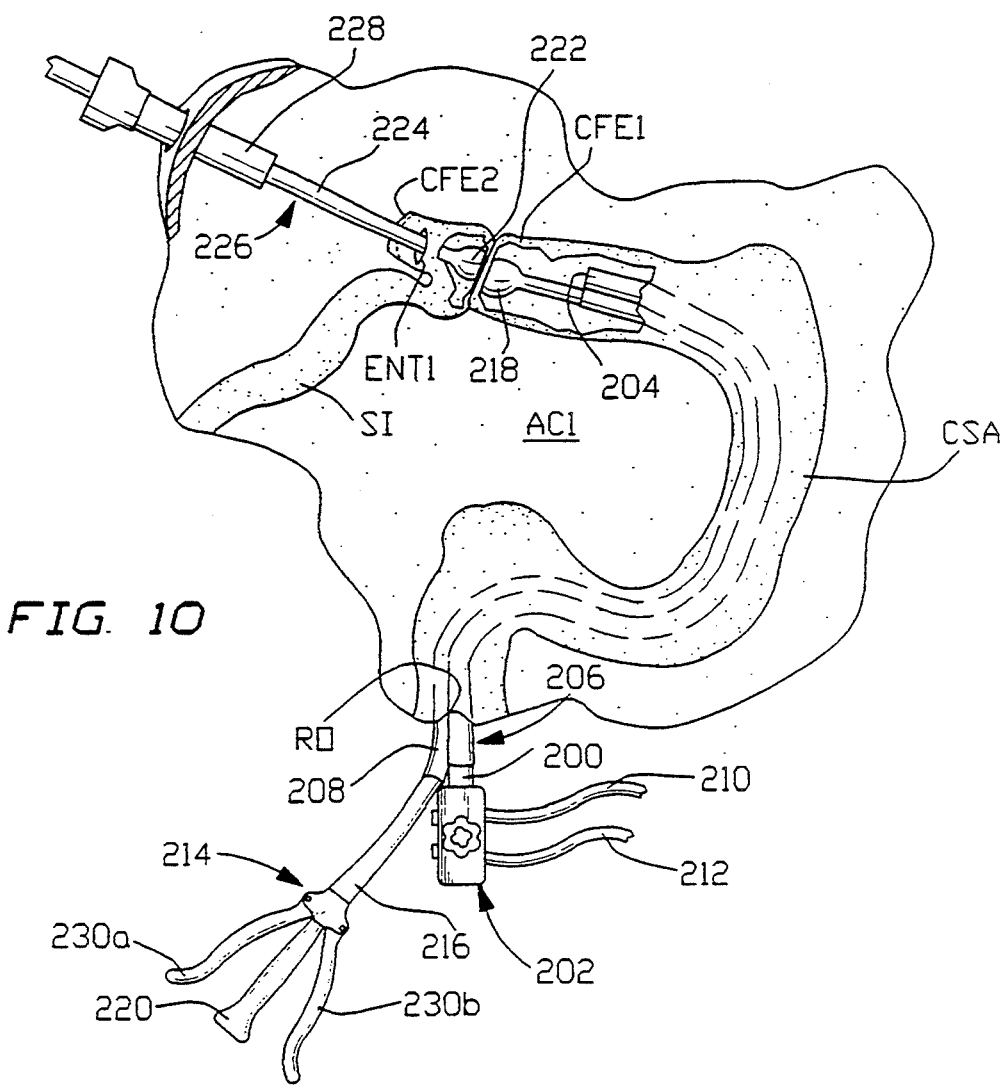
FIG. 10 is a partial broken-away schematic view of a patient's abdomen during a step in a combination laparoscopic and endoscopic anastomosis procedure in accordance with the present invention.

FIG. 10 illustrates a step in a combination laparoscopic and endoscopic anastomosis procedure. During an initial stage of the procedure, an elongate flexible insertion member 200 of an endoscope 202 is inserted through a patient's rectal orifice RO so that a distal end 204 of the insertion member 200 is positioned proximately to a closed free end CFE1 of a colon segment CSA. End CFE1 has been previously closed, for example, by a laparoscopic gastro-intestinal anastomosis stapling device (not shown) or by a purse-string suture applied by the laparoscopic instrument of FIGS. 4, 5 and 6A-6C. Endoscope insertion member 200 is encased by a sheath 206 provided with at least one expandable channel 208. Such a sheath is disclosed in Silverstein et al. U.S. Pat. Nos. 4,646,722 and 5,025,778, the disclosures of which are hereby incorporated by reference.

Endoscope 202 includes a fiber optic illumination guide 210 for guiding light from the proximal end to the distal end of the scope. An image guide 212 is provided in insertion member 200 for transmitting an image from the distal end of the insertion member to the proximal end of endoscope 202. Illumination guide 210 extends from an illmination source (not illustrated), while image guide 212 extends to a video camera (not illusttrated) which in turn is connected to a video monitor (not shown) in conformity with existing endoscopic instrumentation.

Upon the disposition of insertion member distal end 204 so that closed segment end CFE1 is visually detectible via the endoscope's optical elements, a stapling device 214 is inserted through biopsy channel 208. Stapling device 214 includes a flexible shaft 216 and a stapling member 218 at a distal end of the shaft. A first actuator 220 in the form of a rotatable mandrel is disposed at a proximal end of shaft 216 and is operatively connected to stapling member 218 for moving an anvil member 222 and the stapling member towards one another to clamp free end CFE1 of colon segment CSA to an iliac segment SI.

Anvil member 222 is connected to the distal end of an elongate shaft 224 of a stapling instrument 226 which cooperates with stapling device 214 in forming an anastomosis between colon segment CSA and iliac segment SI. Anvil member 222 and a distal end portion of shaft 224 are inserted into a patient's abdominal cavity AC1 through a trocar sleeve 228 traversing an abdominal wall AW1. Anvil member 222 is subsequently inserted into iliac segment SI through an incision or enterotomy ENT1 formed in the wall of iliac segment SI.

Iliac segment SI has an end CFE2 which has been previously closed, for example, by a laparoscopic gastrointestinal anastomosis stapling device (not shown) or by a purse-string suture applied by the laparoscopic instrument of FIGS. 4, 5 and 6A-6C. Iliac segment SI is juxtaposed to free end CFE1 in a side-to-end configuration prior to a staple firing operation. The juxtaposition may be effectuated or facilitated via laparoscopic grasping instruments (not shown) and stapling instrument 226 may be manipulated in part to position iliac segment SI after the insertion of anvil member 222 through enterotomy ENT1.

Upon a juxaposition of stapling member 218 and anvil member 222, actuator 220 is turned to eject a screw connector (not shown) from stapling member 218 through the walls of colon segment CSA and iliac segment SI towards anvil member 22 to connect with the anvil member and to draw it towards the stapling member so that the walls of colon segment CSA and iliac segment SI are clamped or sandwiched therewbetween, as shown in FIG. 10.

Stapling device 214 also has a second actuator in the form of two hand grips 230a and 230b, disposed at a proximal end of shaft 216 and operatively connected to stapling member 218, for ejecting a plurality of staples (not shown) essentially simultaneously from the stapling member towards anvil member 222 upon a clamping of organ segments CSA and SI. The staples are configured preferably in two circular endless arrays, as in conventional rigid end-to-end or intra-luminal anastomosis stapling devices. The staples are oriented in an axial direction relative to shaft 216 and are ejected from stapling member 218 in the axial direction.

Figure 11:
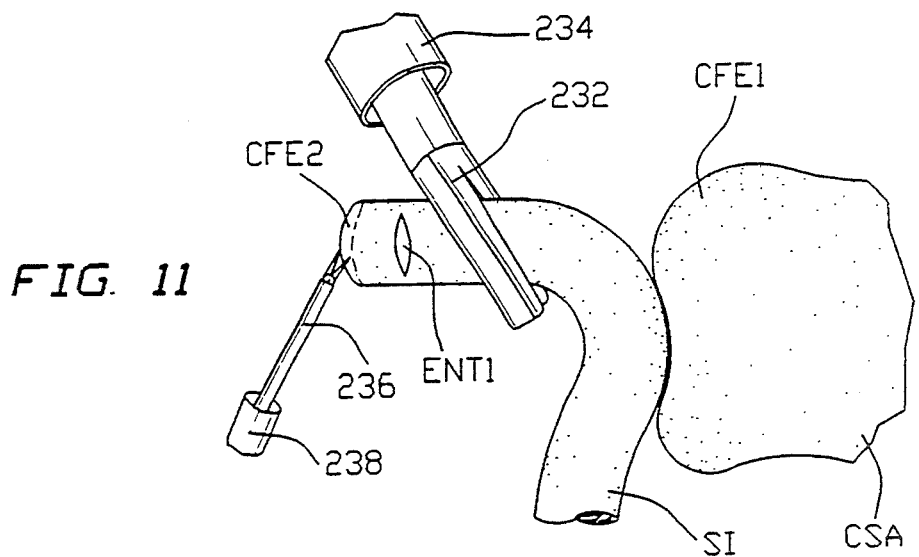
FIG. 11 is a partial schematic view of intestinal organ segments connected to one another in an anastomosis procedure in accordance with the present invention, showing a step subsequent to that illustrated in FIG. 10.

Upon a completion of stapling and a concomitant cutting of the walls of colon segment CSA and iliac segment SI inside the circular staple arrays, actuator 220 is turned to release anvil member 222 from stapling member 218. Anvil member 222 is then withdrawn from iliac segment SI via enterotomy ENT1, while stapling member 218 is extracted from colon segment CSA via rectal orifice RO. As illustrated in FIG. 11, the free end of iliac segment SI may be severed by a laparoscopic gastro-intestinal anastomosis stapling device 232 inserted through a trocar sleeve 234. A laparoscopic grasping forceps 236 inserted through another trocar sleeve 238 is used to hold the severed iliac section and remove it from the abdomen. A laparoscopic specimen retrieval device may be used to facilitate extraction of the severed iliac section. Such a device is disclosed in Wilk U.S. Pat. No. 5,074,867, the disclosure of which is hereby incorporated by reference herein.

Figure 12:
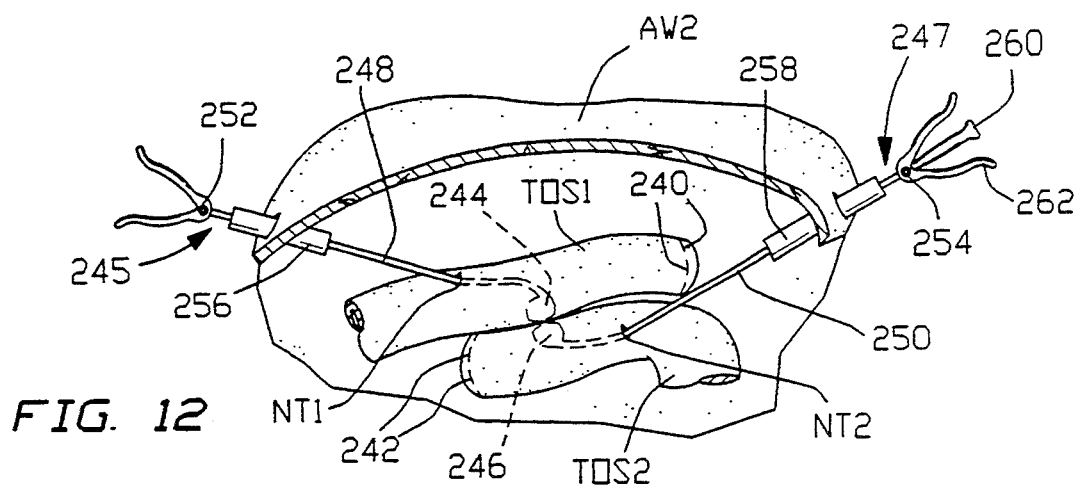
FIG. 12 is a partial broken-away schematic view of a patient's abdomen during a step in a laparoscopic anastomosis procedure in accordance with the present invention.

As illustrated in FIG. 12, two tubular organ segments TOS1 and TOS2 are joined in a side-to-side configuration in a laparoscopic anastomosis operation. Each organ segment TOS1 and TOS2 has been previously closed at a free end by a respective purse-string-type suture 240 or 242 applied, for example, by the instrument of FIGS. 4, 5, and 6A-6C. Alternatively, the free ends of organ segments TOS1 and TOS2 may be closed by staples ejected by a linear gastro-intestinal anastomosis stapling device (not shown).

In the laparoscopic anastomosis operation illustrated in part in FIG. 12, laparoscopic stapling members 244 and 246 of respective laparoscopic stapling devices 245 and 247 are inserted into organ segments TOS1 and TOS2 via respective incisions or enterotomies NT1 and NT2 formed in the side walls of the organ segments. Incisions or enterotomies NT1 and NT2 may be formed by laparoscopic scalpels (not shown). Laparoscopic stapling members 244 and 246 are fixed to the distal ends of respective shafts 248 and 250 which are preferably flexible, at least along distal end portions, for facilitating the positioning and alignment of the stapling members inside organ segments TOS1 and TOS2. The distal end portions of shafts 248 and 250 are controllable, that is, a surgeon can adjust the orientations of the stapling members 244 and 246 by manipulating actuators 252 and 254 from outside of the patient. Actuators 252 and 254 may be rotary knobs connected to tension cables (not shown) extending along shafts 248 and 250. Alternatively, actuators 252 and 254 may be joysticks which are connected to control inputs of electric motors (not illustrated) for selectively tensioning directional cables.

As further illustrated in FIG. 12, the distal ends of shafts 248 and 250 are inserted into a patient via respective laparoscopic trocar sleeves 256 and 258 which traverse an abdominal wall AW2. Upon insertion of stapling memebrs 24 and 246 into organ segments TOS1 and TOS2, stapling devices 245 and 247 may be used to position the organ segments in a desired side-to-side configuration. Alternatively or additionally, laparoscopic grapsing forceps (not shown) may be used to manipulate organ segments TOS1 and TOS2 into the desired relative positions.

One stapling member, e.g., stapling member 246, contains anastomosis staples (not shown), while stapling member 244 is an anvil member for assisting in the bending of the staple legs during a staple ejection step. Upon a positioning of anvil memebr 244 and stapling member 246, as well as organ segments TOS1 and TOS2, a spindle actuator 260 at the proximal end of device 247 may be turned to eject a threaded connector from stapling member 246 into anvil member 244, thereby clamping organ segments TOS1 and TOS2 between anvil member 244 and stapling member 246. Actuator hand grips 262 are then squeezed to eject staples (not shown) in an axial direction from the distal end of stapling member 246.

Upon the completion of the stapling operation (including cutting of an opening inside an endless staple array), anvil member 244 and stapling member 246 are detached from one another and withdrawn from organ segments TOS1 and TOS2 via enterotomies NT1 and NT2. The enterotomies NT1 and NT2 are closed by stapling, or suturing, as described hereinabove with reference to FIGS. 10 and 11. Alternatively, an enterotomy may be closed by a double balloon closure device as described and illustrated in allowed U.S. patent application Ser. No. 803,582 filed Dec. 9, 1991, the disclosure of which is hereby incorporated by reference.

Figure 13:
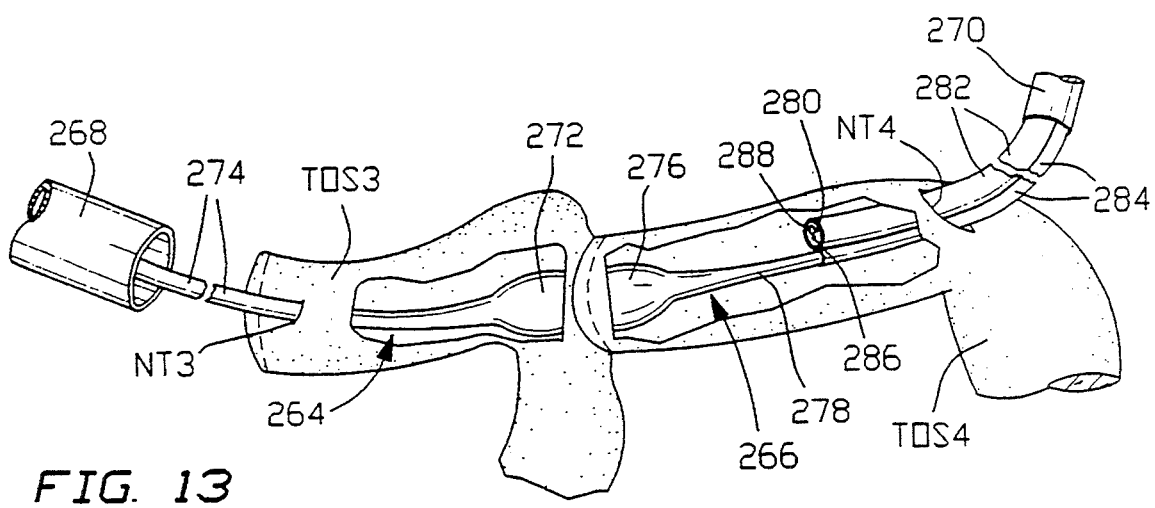
FIG. 13 is a side elevational view of a pair of intestinal segments in a side-to-end anastomosis operation in accordance with the present invention, showing a pair of cooperating laparoscopic anastomosis stapling devices.

FIG. 13 depicts a side-to-end anastomosis between two tubular organ segments TOS3 and TOS4, e.g., intestines, accomplished via a laparoscopic procedure. Laparoscopic anastomosis stapling devices 264 and 266 are inserted into a patient's abdominal cavity via laparoscopic trocar sleeves 268 and 270. An anvil member 272 at the distal end of a shaft 274 of stapling device 264 is inserted into organ segment TOS3 through an enterotomy NT3, while a stapling member 276 at the distal end of a shaft 278 of stapling device 266 is inserted into organ segment TOS4 through an enterotomy NT4. At least one stapling device, e.g., device 266, is inserted into the patient's abdominal cavity with a laparoscope 280 provided with a sheath 282 having a channel or ancillary tube 284. Stapling device 266 longitudinally traverses channel 284. A light guide 286 conveys light to the abdominal cavity, while an image guide 288 transmits a visually detectable image to a camera and monitor (neither shown).

Clamping of organ segments TOS3 and TOS4 by anvil member 272 and stapling member 276 is accomplished as described hereinabove with reference to FIG. 12. The completion of the anastomosis operation is also similar to that described above. It is to be noted that the anvil members and stapling members used in the operations depicted in FIGS. 10, 12, and 13 may be clamped to one another via annular magnets (not shown). Such magnetic clamping is described in detail hereinafter with reference to additional embodiments of the invention.

Figure 15:
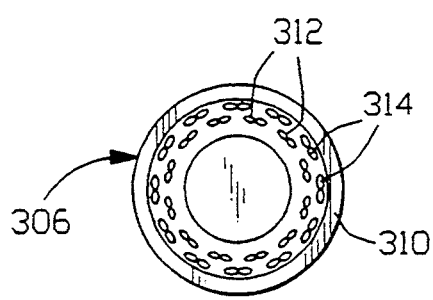
FIG. 15 is a front elevational view of an anvil member of the stapling device of FIG. 14.
Figure 16:
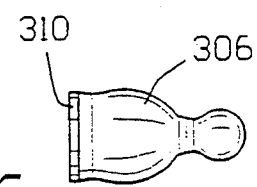
FIG. 16 is a side elevational view of the anvil member of FIGS. 14 and 15.
Figure 14:
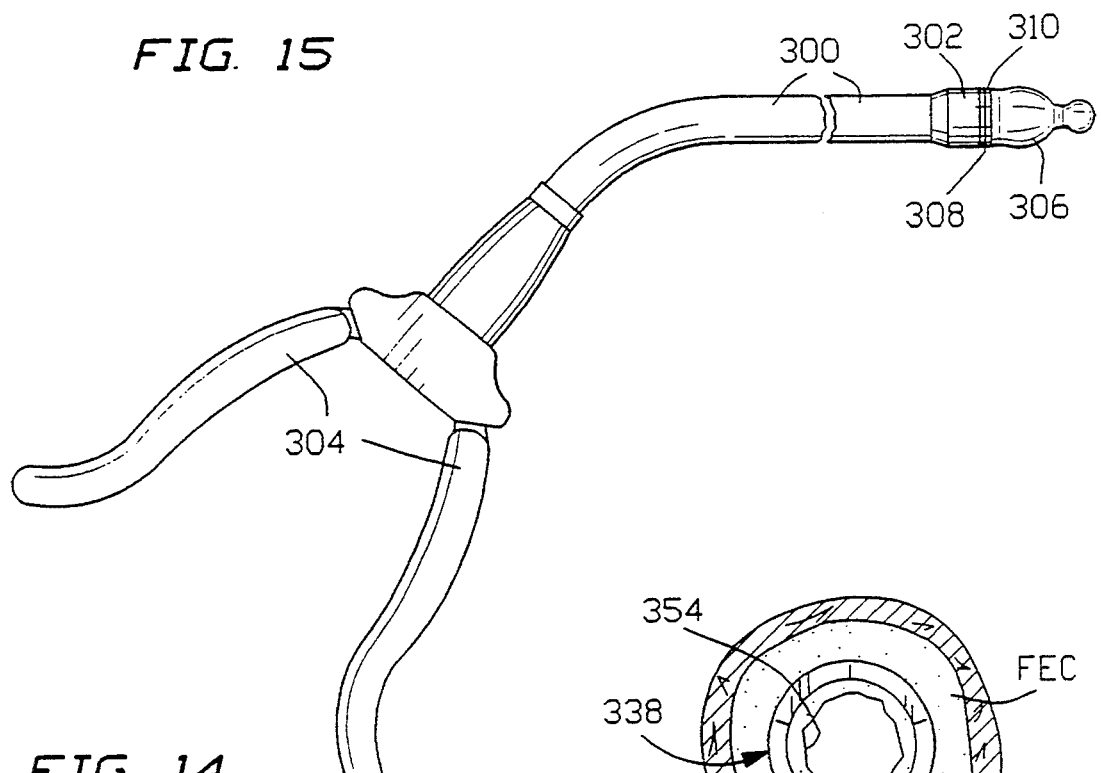
FIG. 14 is a side elevational view of an anastomosis stapling device in accordance with the present invention.

As illustrated in FIGS. 14, 15, and 16, an anastomosis stapling device comprises a shaft 300, which may be flexible or rigid, a stapling member 302 at a distal end of the shaft, and a pair of hand grip actuators 304 at a proximal end of the shaft. Hand grip actuators 304 are connected to a staple ejection mechanism (not shown) in stapling member 302 for operating the mechanism to eject a plurality of anastomosis staples in an axial direction towards an anvil member 306 held to stapling member 302 by a pair of annular magnetic elements 308 and 310 respectively attached to stapling member 302 and anvil member 306. Anvil member 306 includes two circular arrays of depressions 312 and 314 located coaxially within magnetic element 310. One magnetic element 308 or 310 may be a permanent magnet, while the other magnetic element 310 or 308 is a magnetizable metal. Magnetic elements 308 and 310 clamp stapling member 302 and anvil member 306 to one another, thereby sandwiching organ walls during an anastomosis stapling operation.

Figure 17C:
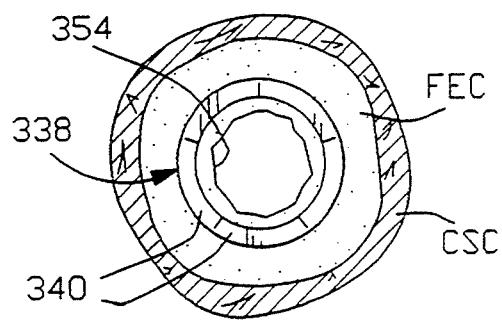
FIG. 17C is a transverse cross-secitonal view taken along line XVII—XVII in FIG. 17B.
Figure 17B:
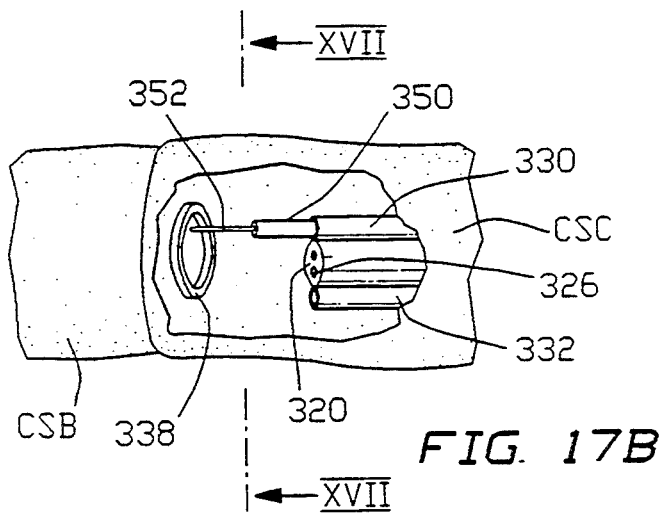
FIGS. 17B is a partial side elevational view showing a subsequent step in the endoscopic anastomosis stapling operation illustrated in part in FIG. 17A.
Figure 17A:
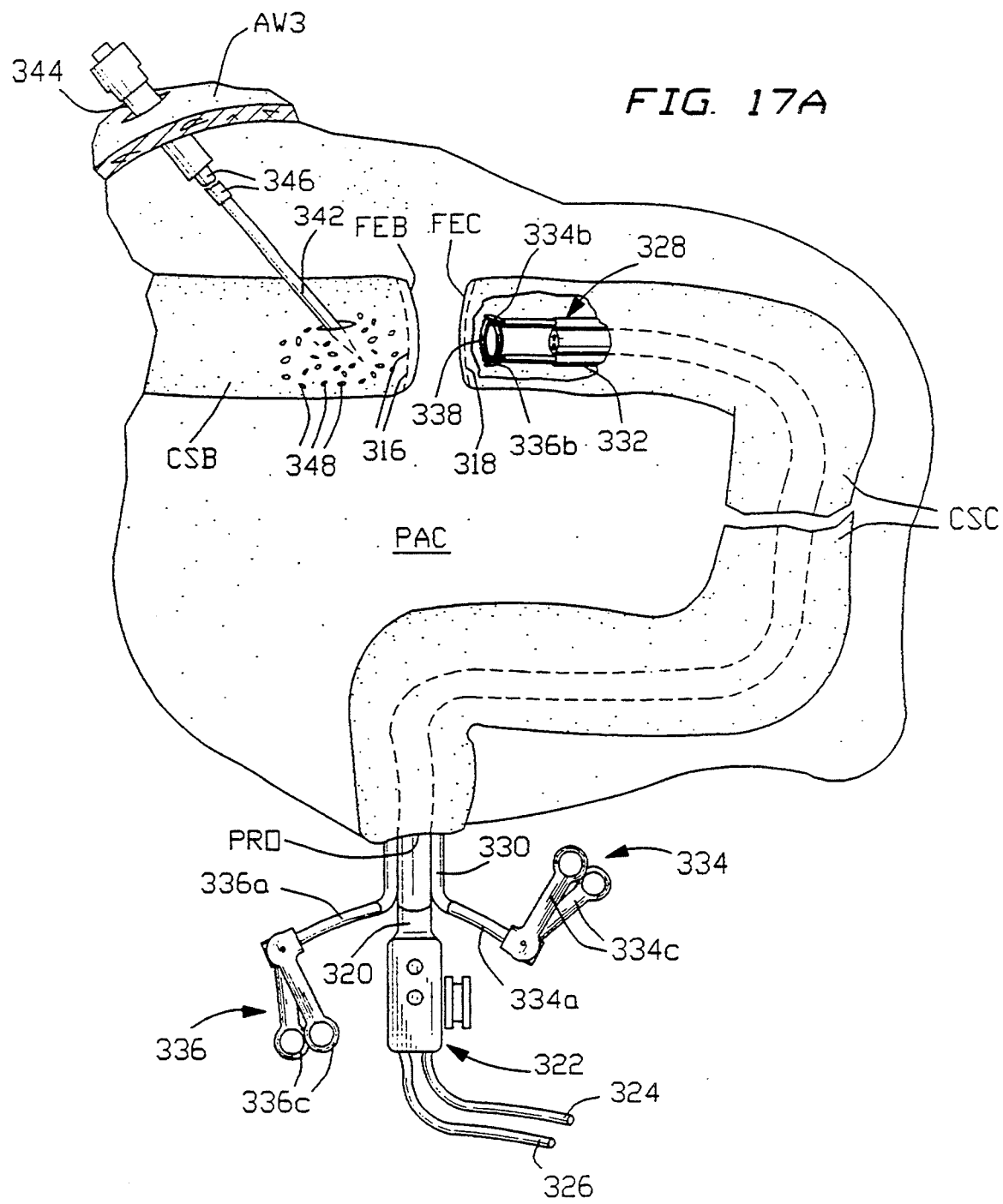
FIG. 17A is a side elevational view of an endoscopic anastomosis stapling assembly in accordance with the present invention, showing the assembly during a step in an anastomosis stapling operation in accordance with the present invention.

FIG. 17A illustrates a step in a magnetically implemented laparoscopic and endoscopic anastomosis operation. Upon a bowel ressection, first and second colon segments CSB and CSC are closed at respective free ends FEB and FEC via purse-string sutures or linear staple arrays 316 and 318. A flexible insertion member 320 of an endoscope 322 is inserted through the patient's rectal orifice PRO into colon segment CSC. During the insertion of insertion member 320, light is transmitted into colon segment CSC via an illumination guide 324. An image is transmitted to a camera and monitor (neither shown) via a fiberoptic image guide 326.

A sheath 328 provided on endoscope insertion member 320 has a plurality of expandable biopsy channels 330 and 332 for receiving a pair of endoscopic grasping forceps 334 and 336 having flexible shafts 334*a* and 336*a* and grasping jaws 334*b* and 336*b* at distal ends of the shafts. A flexible magnet 338 having a spring bias tending to form the magnet into a ring is loaded into one of the biopsy channels 330 and 332 and ejected distally upon the visual detection of the closed end FEC of colon segment CSC. Magnetic 338 may be formed of a plurality of arcuate sections 340 hingedly secured to one another, as illustrated in FIG. 17C. Upon an ejection of magnet 228 from a distal end of a biopsy channel 330 or 332 and upon expansion of the magnet from a collapsed configuration to an annular configuration, actuator handles 334*c* and 336*c* of grasping forceps 334 and 336 are manipulated to manuever magnet 338 to a desired position inside colon segment CSC.

In a laparoscopic step of the anastomosis operation, a hollow needle 342 is inserted into the patient's abdominal cavity PAC via a trocar sleeve 344 disposed in the abdominal wall AW3. Needle 342 is part of a syringe 346 containing magnetic particles 348, for example, iron pellets, beads, or rods. The magnetic particles 348 are ejected into colon segment CSB, as shown in the drawing, and are attracted to the end wall (in an end-to-end anastomosis) by virtue of a magnetic force field generated by magnet 338.

Upon a consequent clamping of the walls of colon segments CSB and CSC by the magnetic forces between magnet 338 and particles 348, grasping forceps 334 and 336 are withdrawn from channels 330 and 332. Subsequently, as illustrated in FIG. 17B, an optical fiber 350 is inserted through one of the channels, e.g., channel 330. A laser beam 352 transmitted along fiber 350 is aimed at the clamped colon wall inside magnet 338. Optical fiber 350 may be provided with longitudinally extending tensioning wires (not shown) for controlling the distal end orientation of the fiber, thereby controlling the direction of propagation of laser beam 352. Laser beam 352 is thus used to cut a circular hole 354 in closed ends FEB and FEC of colon segments CSB and CSC, as depicted in FIG. 17C.

Of course, laparoscopic graspsing forceps (not illustrated) may be used to position colon segments CSB and CSC during the magnetically implemented laparoscopic and endoscopic anastomosis operation of FIGS. 17A-17C. Magnet 338 and magnetic particles or elements 348 remain inside the connected bowel subsequently to the extraction of endoscope insertion member 320. The magnetic forces serve to hold colon segments CSB and CSC to one another during a knitting or growing together of the organic tissues. The magnetic elements fall out eventually, when the clamped tissue portions are severed due to necrosis.

If necessary, instead of magnetic or magnetizable particles 348, an ancillary ring (not illustrated) may be inserted into colon segment CSB via a laparoscopic technique.

FIGS. 18A-18D illustrate successive steps in an endoscopic end-to-end or intraluminal anastomosis. It is to be noted that a side-to-side or end-to-side anastomosis could be performed by essentially the same technique.

Several days prior to the anastomosis operation, the patient P swallows a weight 356 to which a string 358 is attached. Upon the passage of the weight through the digestive tract DT, as illustrated in FIG. 18A, the colon CN is severed along a line A-A and the small intestine SMI is severed along a line B—B. This severing may be implemented via a gastrointestinal anastomosis stapling device (not shown), which may be a laparoscopic device or one used in conventional open abdominal surgery. If the operation is laparoscopic, then the pursestring-suturing device of FIGS. 4-6C may be used to close the free ends of the severed bowel sections.

Upon the severing of colon CN along line A—A and small intestine SMI along line B—B, a bowel section BS containing a cancerous growth CG is removed. If the operation is laparoscopic, severed bowel section BS may be placed in a bag (not shown) and macerated or sectioned inside the bag for removal through a laparoscopic trocar sleeve, in a procedure described in U.S. Pat. No. 5,074,867, the disclosure of which is hereby incorporated by reference. Of course, a large incision may be made in the abdominal wall for removing the severed bowel section BS in its entirety.

In order to join colon CN and small intestine SMI along their closed free ends, as depicted in FIGS. 18B-18D, a first endoscope insertion member 360 is inserted through the patient's mouth PM (FIG. 18A), the esophagus ES, the stomach ST and small intestine SMI to the free end thereof. As illustrated in FIGS. 18B-18D, endoscope insertion member 360 is enveloped with a cylindrical sheath 362 provided with at least one expandable channel or tube 364 in a collapsed configuration.

Endoscope insertion member 360 has a fiberoptic illumination guide 366 and a fiberoptic image guide 368 which are used to trace string 358 during the insertion of endoscope insertion member 360 through the upper portion of the patient's digestive tract DT. When the distal end of insertion member 360 reaches the closed free end of small intestine SMI, an anastomosis anvil member 370 attached to the distal end of a flexible shaft 372 is inserted through channel 364, thereby expanding the channel from the collapsed configuration.

A second endoscope insertion member 374 is inserted through the patient's anus PA (FIG. 18A), and colon CN to the free end thereof. As illustrated in FIGS. 18B-18D, endoscope insertion member 374 is enveloped with a cylindrical sheath 376 provided with at least one expandable channel or tube 378 in a collapsed configuration.

Endoscope insertion member 374 has a fiberoptic illumination guide 380 and a fiberoptic image guide 382 which are used to trace string 358 during the insertion of endoscope insertion member 374 through the lower portion of the patient's digestive tract DT. When the distal end of insertion member 374 reaches the closed free end of colon CN, an anastomosis stapling member 384 attached to the distal end of a flexible shaft 386 is inserted through channel 378, thereby expanding the channel from the collapsed configuration.

Upon the exit of stapling member 384 from channel 378, a sharp screw connector 388 (FIG. 2) is ejected in the distal direction from the stapling member 384 and pierces the wall of colon CN. Upon further shifting in the distal direction, connector 388 couples with anvil member 370 through the walls of colon CN and small intestine SMI and brings anvil member 370 and stapling member 384 closer to one another to clamp the walls of colon CN and small intestine SMI, as depicted in FIG. 18D.

It is to be noted that screw connector 388 may be replaced with magnetic rings 390 and 392 which are located at the distal ends of anvil member 370 and stapling member 384. The magnetic forces serve in part to facilitate the alignment of anvil member 370 and stapling member 384 during an anastomosis procedure.

Upon the termination of the anastomosis stapling procedure, insertion members 360 and 374 are withdrawn from digestive tract DT.

Figure 19:
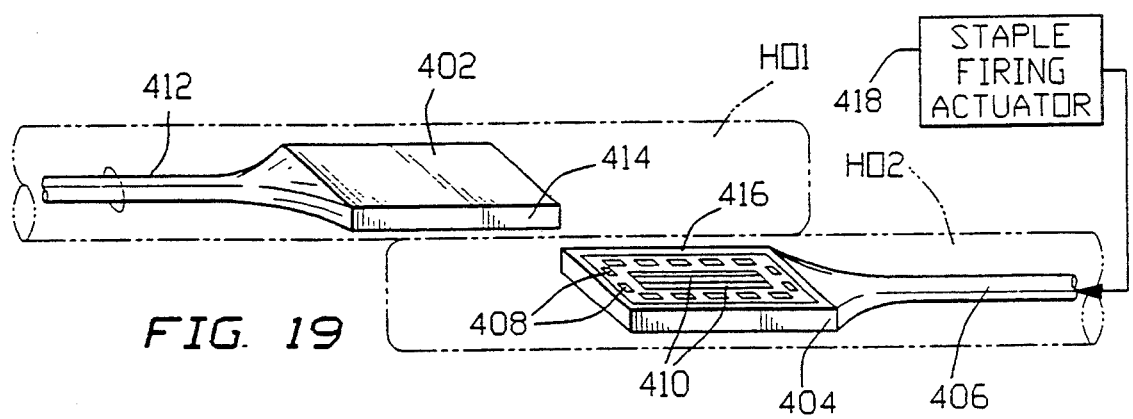
FIG. 19 is a perspective view of an anastomosis stapling assembly in accordance with the present invention, showing an anvil member and a stapling member spaced from one another prior to formation of an anastomosis.

FIG. 19 shows a laparoscopic or endoscopic anvil member 402 and an anastomosis stapling member 404 for cooperating therewith in forming a side-to-side anastomosis between two hollow organs HO1 and HO2. Stapling member 404 is disposed at the distal end of a shaft 406 and is provided with a plurality of staple-containing apertures or recesses 408 arrayed in an endless configuration (e.g., rectangular or oval). In addition, stapling member 404 carries one or more blades 410.

Anvil member 402 is disposed at the distal end of a shaft 412 and is formed with an array of anvil depressions (not shown) in an endless configuration matching that of staple recesses 408. Anvil member 402 and stapling member 404 are additionally provided along facing peripheries with endless magnetic elements 414 and 416 for enabling a clamping of the walls of organs HO1 and HO2. Alternatively, stapling member 404 may be provided with an ejectable screw type connector element (not xhown) for temporarily fastening anvil member 402 and stapling member 404 to one another.

A staple firing actuator or mechanism 418 is operatively connected to stapling member 404 via shaft 406 for ejecting a plurality of staples (not shown) essentially simultaneously (i.e. in quick succession, according to the common technique in the art) from recesses 408. The staples are fired in a common direction oriented essentially transversely to shaft 406 at the distal end thereof. Blades 410 are also shifted in the same lateral or transverse direction.

Figure 20:
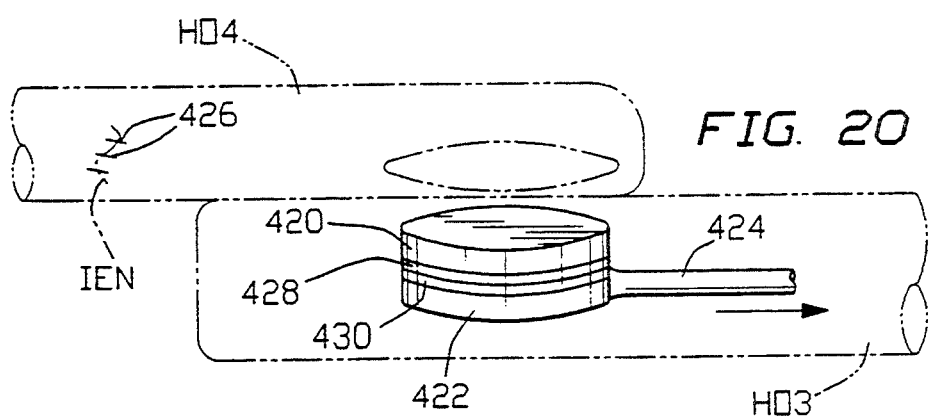
FIG. 20 is a perspective view of another anastomosis stapling assembly in accordance with the present invention, showing an anvil member attached to a stapling member after creation of an anastomosis.

FIG. 20 shows a laparoscopic or endoscopic anvil member 420 and an anastomosis stapling member 422 connected to one another and being withdrawn together through a hollow organ HO3 after forming a side-to-side anastomosis between two hollow organs HO3 and HO4. Stapling member 422 is disposed at the distal end of a shaft 424 and has a structure similar to that described above for stapling member 404.

Anvil member 420 is a free member and has a structure similar to that described above for anvil member 402. Anvil member is inserted inside hollow organ HO4 through an enterotomy IEN which is subsequently closed with stitches or staples 426 or a balloon closure device, as described above. Anvil member 420 may be detachably fastened to the distal end of a laparoscopic instrument and releaased upon insertion through enterotomy IEN.

Anvil member 420 and stapling member 422 are formed along facing surfaces with endless magnetic elements 428 and 430 for enabling a clamping of the walls of organs HO3 and HO4. Alternatively, stapling member 422 may be provided with an ejectable screw type connector element (not shown) for temporarily fastening anvil member 420 and stapling member 422 to one another.

Upon the formation of an anastomosis opening AO between hollow organs HO3 and HO4, anvil member 420 and stapling member 422 are withdrawn together through a hollow organ HO3.

The cooperating anvil members and stapling members of FIGS. 19 and 20 may be used in performing side-to side anastomosis as discussed above with reference to FIGS. 10, 12, 13. In addition, cooperating anvil members and stapling members of FIGS. 19 and 20 may be used in the choledocoduodenostomy procedure described below with reference to FIG. 21.

The common bile duct CBD (FIG. 21) frequently becomes filled with stones (not illustrated) which are too numerous to be removed either through the Papilla of Vater PV or through an incision in the wall of the common bile duct. In such a situation, the gall bladder GB has already been removed and it is desirable to form an anastomosis between the common bile duct CBD and the duodenum DU.

Figure 21:
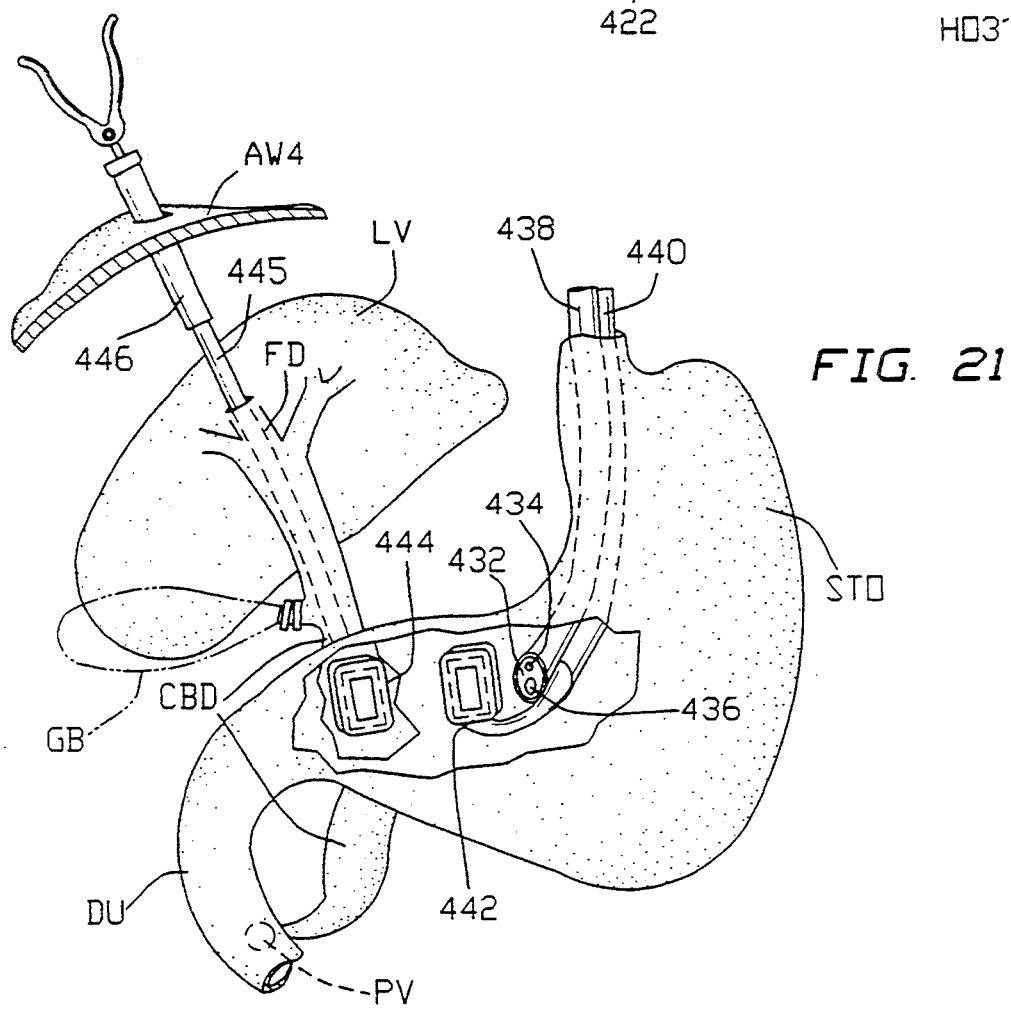
FIG. 21 is a schematic side elevational view, partially broken away, of a person's liver, stomach, and common bile duct with an anastomosis stapling assembly in accordance with the present invention, showing a step in a choledocoduodenostomy in accordance with the present invention.

As illustrated in FIG. 21, an endoscope insertion member 432 with a light guide 434 and an image guide 436 is inserted into the stomach STO from the upper end of the digestive tract. Insertion member 432 is provided with a sheath 438 having an expandable channel 440 through which an anastomosis stapling member 442, such as that described hereinabove with reference to FIGS. 19 and 20, is inserted. A cooperating anastomosis anvil member 444 and the end of a shaft 445 is inserted through a laparoscopic trocar sleeve 446 disposed in an abdominal wall AW4 of the patient. The anvil member 444 is further inserted through the liver LV and into the common bile duct CBD through a feeder duct FD.

Figure 22A:
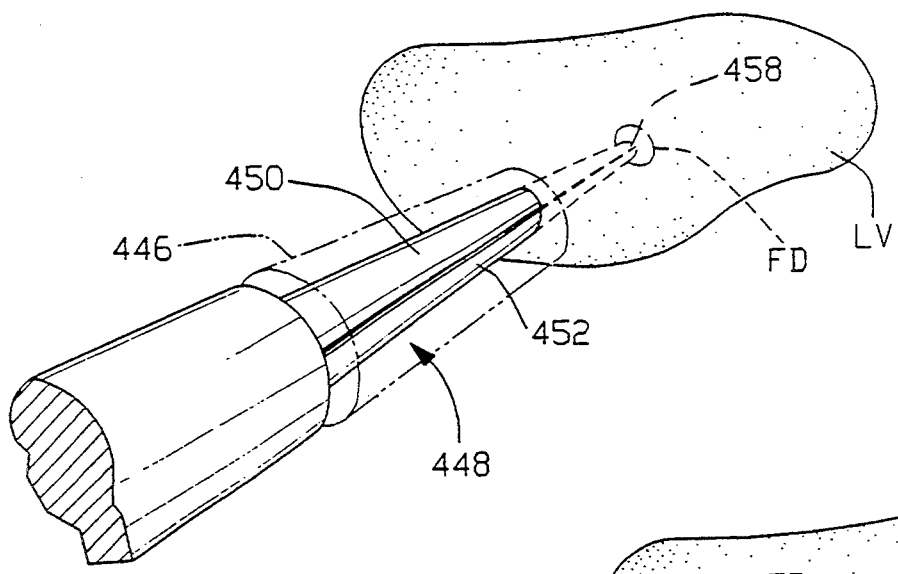
FIGS. 22A-22C illustrate successive steps in the insertion of an anastomosis anvil member through a patient's liver into the common bile duct.
Figure 22B:
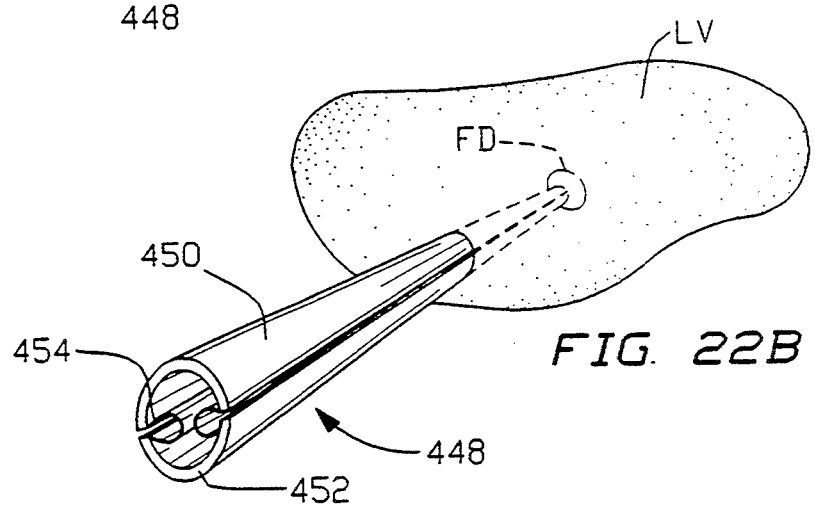
Figure 22C:
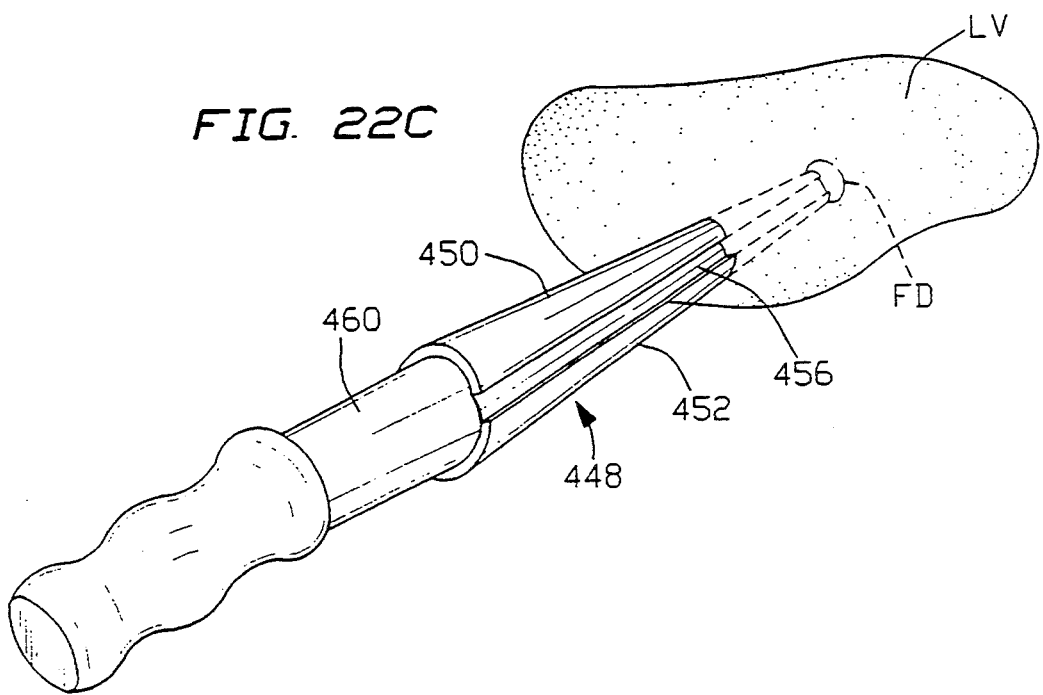

The insertion of anvil member 444 through liver LV and into common bile duct CBD is achieved via use of an expandable dilating device 448, as shown in FIGS. 22A–22C. Dilating device 448 comprises a pair of substantially cylindrical elongate rigid sections 450 and 452 connected to one another along pairs of longitudinally extending edges by two elastic membranes 454 and 456. Membranes 454 and 456, together with sections 450 and 452, define an elongate transversely expandable channel through which a needle 458 is inserted.

In an initial step, needle 458 is inserted through dilating device 448 and then the distal end of the needle and the dilating device are inserted through trocar sleeve 446 (FIG. 21) into liver LV. The site of insertion into liver LV has been previously located by another technique, for example, by visual inspection with a laparoscope (not shown) which is viewing the liver LV through another trocar sleeve (not illustrated). Further information, for example, as to the location of a suitable feeder duct FD, may be obtained by a CAT scan or an MRI process.

Upon the insertion of needle 458 a predetermined distance into the liver LV, needle 458 is removed while maintaining the distal end portion of dilating device 448 inside the organ, as illustrated in FIG. 22B. Subsequently, as shown in FIG. 22C, an expander rod 460 is inserted through dilating device 448. Preferably, a series of expander rods 460 of gradually increasing thickness are successively inserted into dilating device 448, thereby increasing the size of a passage through liver LV without tearing or cutting the tissues of the organ.

Upon a sufficient expansion of dilating device 448, an insertion member of an endoscope or laparoscope (not shown) may be inserted through the expanded or dilated dilating device 448 to check whether a suitable path through a feeder duct FD has been located.

In closing enterotomies in a laparoscopic or endoscopic anastomosis method as described hereinabove, an endoscopic stapling device as disclosed in Nakao et al. U.S. Pat. No. 5,015,249 may be used. U.S. Pat. No. 5,015,249 discloses an endoscopic stapler which is inserted down a biopsy channel of an endoscope or laparoscope to staple internal body tissues at the distal end of the endoscope insertion member or laparoscope. Other laparoscopic or endoscopic stapling devices may also be used. In addition, an endoscopic suturing device disclosed in Wilk et al. U.S. Pat. No. 5,037,433 may be utilized to close an enterotomy in an anastomosis procedure as described herein. U.S. Pat. Nos. 5,015,249 and 5,037,433 are hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. For example, although the suture needle guide device 110 of FIGS. 4 and 5 is disclosed as having a pair of jaws 114 and 116 for clamping a tubular organ, it is possible that a seam in organic tissues may be effectuated by pressing a single elongate member with recesses against the subject tissues and threading a suture needle through passages in the elongate member and through the tissues ensconced in the recesses. This operation could be performed laparoscopically or in an open-incision procedure.

The formation of purse-string-type sutures at the free ends of intestinal segments SC1 and SC2 may be acheived by other equivalent techniques. For example, needle 130 may be inserted through jaw 114 of instrument assembly 110 by forceps 146 instead of being ejected by a plunger 140.

Accordingly, it is to be understood that the drawings and descriptions herein are proffered by way of example to facilitate comprehension of the invention and should not be construed to limit the scope thereof.

What is claimed is:

1. A surgical method for performing an anastomosis, comprising the steps of:
    disposing a laparoscopic trocar sleeve in a patient's abdominal wall;
    inserting a distal end of a laparoscopic instrument into an abdominal cavity of the patient through said trocar sleeve;
    manipulating said instrument from outside the patient to loop a purse-string-type suture through a free end of a first severed intestinal segment of the patient;
    moving a flexible anastomosis-forming device through the patient's rectum so that an end cap at a distal end of said anastomosis device protrudes from a free end of a second severed intestinal segment of the patient;
    shifting said anastomosis-forming device further through the patient's rectum so that said end cap is inserted into said first severed intestinal segment through the free end thereof;
    during said step of shifting, holding said first severed intestinal segment with a laparoscopic tool from outside the patient to facilitate insertion of said end cap into said first severed intestinal segment;
    upon insertion of said end cap into said first severed intestinal segment, drawing said purse-string-type suture via a laparoscopic member to close the free end of said first severed intestinal segment about said end cap; and
    operating said anastomosis-forming device from outside the patient to connect said first and said second severed intestinal segment to one another in an anastomosis.

2. The method defined in claim 1, further comprising the step of using an endoscopic visual system to visually inspect said second severed intestinal segment internally prior to said step of shifting.

3. The method defined in claim 2 wherein said step of using is performed during said step of moving, said endoscopic visual system being entrained to said anastomosis-forming device during said step of moving.

4. The device defined in claim 2 wherein said step of using is performed prior to said step of moving, said endoscopic visual system being attached to a sheath member with an expandable biopsy-type channel, said step of moving including the step of moving said anastomosis-forming device through said channel.

5. The method defined in claim 1 wherein said laparoscopic instrument comprises a laparoscopic grasping forceps, said step of manipulating including the steps of holding a needle inside the patient's abdominal cavity and maneuvering said needle with said forceps.

6. The method defined in claim 5, further comprising the steps of inserting a laparoscopic clamp into the patient's abdominal cavity and clamping said first severed intestinal segment with said clamp, said step of maneuvering including the step of threading said needle through passages in said clamp.

7. The method defined in claim 1 wherein said laparoscopic instrument comprises a laparoscopic clamp provided with recesses for receiving tissues of said first severed intestinal segment and passages for enabling the threading of a needle and suture through the tissues received in said recesses, further comprising the step of threading said needle through said passages and the tissues tissues received in said recesses.

8. The method defined in claim 1 wherein said end cap comprises an anvil member of said anastomosis-forming device, said step of operating said anastomosis-forming device including the step of ejecting staples from a stapling portion of said anastomosis-forming device towards said anvil member upon a shifting of said first and said second severed intestinal segment towards one another to clamp said first and said second severed intestinal segment to one another.

9. The method defined in claim 1, further comprising the step, performed prior to said step of shifting, of manipulating said instrument from outside the patient to loop an additional purse-string-type suture through a free end of said second severed intestinal segment of the patient, also comprising the step of drawing said additional purse-string-type suture via a laparoscopic member to close the free end of said second severed intestinal segment about said stapling member, upon an ejection of said end cap from said second severed intestinal segment.

* * * * *